(12) United States Patent  
Haiml et al.

(10) Patent No.: US 7,545,494 B2  
(45) Date of Patent: Jun. 9, 2009

(54) ANALYTICAL SYSTEM AND METHOD FOR ANALYZING NONLINEAR OPTICAL SIGNALS

(75) Inventors: Markus Haiml, Zürich (CH); Laurent P. Balet, Grimisuat (CH); Gert L. Duveneck, Bad Krozingen (DE); Gerd Marowsky, Göttigen (DE)

(73) Assignee: Bayer Technology Services GmbH, Leverkusen (DE)

( * ) Notice: Subject to any disclaimer, the term of this patent is extended or adjusted under 35 U.S.C. 154(b) by 276 days.

(21) Appl. No.: 10/565,909

(22) PCT Filed: Jul. 1, 2003

(86) PCT No.: PCT/EP04/07176

§ 371 (c)(1),  
(2), (4) Date: Sep. 5, 2006

(87) PCT Pub. No.: WO2005/019821

PCT Pub. Date: Mar. 3, 2005

(65) Prior Publication Data

US 2006/0291772 A1    Dec. 28, 2006

(30) Foreign Application Priority Data

Jul. 23, 2003    (CH) ..................... 1305/03

(51) Int. Cl.  
    *G01N 21/64*    (2006.01)
(52) U.S. Cl. ............ 356/317; 356/318; 250/458.1
(58) Field of Classification Search ........... 356/317, 356/318; 250/458.1, 459.1, 461.1, 461  
    See application file for complete search history.

(56) References Cited

U.S. PATENT DOCUMENTS 4,245,800 A    1/1981    Henderson ............... 244/3.13

(Continued)

FOREIGN PATENT DOCUMENTS

WO    95/33197 A1    12/1995

(Continued)

OTHER PUBLICATIONS

Science, 248, Apr. 6, 1990, pp. 73-76, Winfried Denk et al, "Two-Photon Laser Scanning Fluorescence Microscopy".

(Continued)

*Primary Examiner*—F. L Evans  
(74) *Attorney, Agent, or Firm*—Wenderoth, Lind & Ponack, L.L.P.

(57) ABSTRACT

A method for the ultrasensitive simultaneous measurement of nonlinear optical emission signals in one or two local dimensions wherein excitation light is irradiated in modulated form from at least one light source into an interactive space in which one or several emissions that are nonlinearly correlated with the excitement light can be excited. The light emanating from the interactive spaces is measured using a one or two-dimensional detector array. Measured data is then transmitted to a computer and formatted in a one or two-dimensional data matrix. Further, non-correlated portions of the light emanating from the interactive spaces that are linearly proportionate to the intensity of the excitement light available in the interactive spaces are separated from portions of the light emanating from the interactive spaces which are not linearly proportionate. The invention also relates to an analytical system for carrying out this method.

88 Claims, 6 Drawing Sheets

U.S. PATENT DOCUMENTS

| | | |
|---|---|---|
| 5,034,613 A | 7/1991 | Denk et al. ............ 250/458.1 |
| 5,445,934 A | 8/1995 | Fodor et al. .................... 435/6 |
| 5,459,574 A | 10/1995 | Lee et al. .................... 356/437 |
| 5,742,355 A | 4/1998 | De Haan et al. ............ 348/607 |
| 5,822,472 A | 10/1998 | Danielzik et al. ............. 385/12 |
| 5,959,292 A | 9/1999 | Duveneck et al. ...... 250/227.11 |
| 6,078,705 A | 6/2000 | Neuschäfer et al. ........... 385/12 |
| 6,122,016 A | 9/2000 | De Haan et al. ............ 348/620 |
| 6,198,869 B1 | 3/2001 | Kraus et al. ................. 385/129 |
| 6,289,144 B1 | 9/2001 | Neuschäfer et al. ........... 385/12 |
| 6,384,912 B2 | 5/2002 | Kraus et al. ................. 356/246 |
| 6,437,345 B1 | 8/2002 | Bruno-Raimondi et al. ...................... 250/458.1 |
| 6,510,263 B1 | 1/2003 | Maisenhölder et al. ........ 385/37 |
| 6,873,764 B2 | 3/2005 | Maisenhoelder et al. ...... 385/37 |
| 6,961,490 B2 | 11/2005 | Maisenholder et al. ........ 385/37 |
| 7,060,957 B2 | 6/2006 | Lange et al. ............. 250/208.1 |
| 2001/0001021 A1 | 5/2001 | Kraus et al. .................... 385/12 |
| 2002/0076154 A1 | 6/2002 | Maisenhoelder et al. ...... 385/37 |
| 2002/0182631 A1 | 12/2002 | Schurmann-Mader et al. . 435/6 |
| 2003/0091284 A1 | 5/2003 | Maisenholder et al. ........ 385/37 |
| 2003/0108291 A1 | 6/2003 | Duveneck et al. ............. 385/37 |
| 2003/0148542 A1 | 8/2003 | Pawlak et al. ............... 436/518 |
| 2003/0186914 A1 | 10/2003 | Hofer et al. .................... 514/44 |
| 2004/0004194 A1* | 1/2004 | Amblard et al. .......... 250/458.1 |
| 2004/0008394 A1 | 1/2004 | Lange et al. ................. 359/237 |
| 2004/0038386 A1 | 2/2004 | Zesch et al. .............. 435/287.2 |
| 2004/0052489 A1 | 3/2004 | Duveneck et al. ........... 385/130 |
| 2004/0058385 A1 | 3/2004 | Abel et al. ................... 435/7.1 |

FOREIGN PATENT DOCUMENTS

| | | |
|---|---|---|
| WO | 00/71028 | 11/2000 |
| WO | 01/13096 A1 | 2/2001 |
| WO | 02/46756 A1 | 6/2002 |
| WO | 02/054071 | 7/2002 |

OTHER PUBLICATIONS

Applied Physics, B, 73 (month unavailable) 1990, pp. 869-871, G.L. Duveneck et al, "Evanescent-field-induced two-photon fluorescence: excitation of macroscopic areas of planar waveguides".

Analytica Chimica Acta, 469, (month unavailable) 2002, pp. 49-61, Gert L. Duveneck et al, "Planar waveguides for ultra-high sensitivity of the analysis of nucleic acids".

Peregrinus, 232, (month unavailable) 1983, pp. 1-30, M.L. Meade, "Lock in amplifiers: principles In applications".

IEEE Journal of Quantum Electronics, vol. 31, No. 9, Sep. 1995, pp. 1705-1708, T. Spirig et al, "The Lock-In CCD-Tow-Dimensional Synchronous Detection of Light".

IEEE Transactions of Electron Devices, vol. 44, No. 10, Oct. 1997, pp. 1643-1647, Thomas Spirig et al, "The Multitap Lock-In CCD with Offset Subtraction".

J. Opt. Soc. Am. A, vol. 18, No. 8, Aug. 2001, pp. 1972-1979, Arnaud Dubois, "Phase-map measurements by interferometry with sinusoidal phase modulation and four integrating buckets".

Applied Optics, vol. 41, No. 4, Feb. 2002, pp. 805-812, Arnaud Dubois et al. "High-resolution full-field optical coherence tomography with a Linnik microscope".

Barry N P et al: "Applications of ultrafast lasers to two-photon fluorescence and lifetime imaging" Proceedings of the Spie—The International Society for Optical Engineering Spie-Int. Soc. Opt. Eng. USA, Bd. 4633, Jan. 23, 2002 Seiten 50-61, XP001203516.

* cited by examiner

ANALYTICAL SYSTEM AND METHOD FOR ANALYZING NONLINEAR OPTICAL SIGNALS

The present invention describes a method for detecting optical signals on which scattered, noise and background signals, for example, are superposed. Specifically, this method is suitable for detecting weak nonlinear optical signals, such as, for example, of luminescence after two-photon excitation, that is to say after simultaneous absorption of two photons having a relatively low energy (relatively long wavelength) by a chromophore capable of luminescence, which leads to the emission of a photon having a higher energy (shorter wavelength) than that of the excitation light in the form of luminescence [W. Denk, J. H. Strickler and W. W. Webb, "Two-photon laser scanning fluorescence microscopy", Science 248 (1990) 73-76; Duveneck, G. L. et al., "Evanescent-field-induced two-photon fluorescence: excitation of macroscopic areas of planar waveguides", Applied Physics B, 73 (2001) 869-871.]

Nonlinear optical signals are characterized in that their signal magnitudes depend nonlinearly on the exciting light intensity. In the case of two-photon luminescence excitation, which presupposes the simultaneous absorption of two photons of the excitation light radiated in, the intensity of the resulting luminescence is proportional to the square of the excitation intensity, in contrast for example to conventional one-photon luminescence excitation, in which the intensity of the emission of low-energy luminescence (longer wavelength) induced after the absorption in each case of a single excitation photon having a higher energy (shorter wavelength) by molecules capable of luminescence is generally linearly dependent on the excitation intensity. Deviations from this linear relationship for the luminescence generated by the absorption in each case of a single photon by a chromophore capable of luminescence occur for example in the case of an inversion of the population numbers of higher-and low-energy excited states (that are typical of the functional principle of a laser) or upon approximation to the saturation of an excited state and to the corresponding depletion of the ground state. A further example of a linear dependence on the intensity of the excitation light radiated in is the intensity of the scattered light from rough surfaces. By contrast, the intensity of background light and the intensity of noise of the measured light signals are uncorrelated with the excitation light in many measuring arrangements.

It is evident in practice that the detection limit for weak light signals, for example of emissions of luminescent labels used for the analytical detection of substances of low concentration in a sample, is often determined by scattered light of the excitation light (e.g. of a laser). Since the luminescent light and the excitation light have different wavelengths, these can be separated spectrally up to a certain degree, for example by means of transmission filters (bandpass filters such as e.g. interference filters or high-pass filters). Particularly in the case of luminescence excited by one-photon absorption, however, a non-negligible portion of scattered light often reaches the detector. The cause is, inter alia, the usually small spectral separation of excitation and luminescence (Stokes shift) and the typically large intensity difference between extremely weak (luminescent) signals and relatively strong scattered light of the excitation light.

It is a primary object of the present invention to remove portions that are uncorrelated and correlated linearly with the intensity of the excitation light from one-, two- or multidimensional images. In this case, a "one-, two- or multidimensional image" is to be understood to mean the recording of the measured light intensities as a function of one, two or more (then typically three) spatial coordinates. This recording may be present in the form of an imaging (e.g. of a photograph whose intensity values are digitized in the course of the further steps of the method according to the invention) or a numerical file, for example in the form of a computer file.

One essential aspect of the present invention is that the separation of different light portions is not effected in wavelength-specific fashion, but rather in accordance with their nonlinear character. Consequently, it is also possible to separate linear and nonlinear light portions (that is to say light portions that are correlated linearly and nonlinearly with the excitation light) at the same wavelength. By means of the method described below, this separation can also be carried in real time for one-, two- or multidimensional images.

The present invention is explained below primarily against the background of luminescence excitation and detection as an example of a widespread detection method in (bio)chemical analysis as an important field of application of the invention. However, the invention can be applied directly to further optical techniques such as, for example, "second harmonic generation" (where radiating in an excitation light having a specific wavelength leads to the emission of a response light having half the wavelength with respect to the wavelength of the excitation light radiated in) and the fields of application thereof and also to further techniques of wholly or partly non-optical character which relate to the detection of signals which follow the intensity of a power-modulated stimulating excitation signal in a nonlinear manner.

TECHNICAL BACKGROUND OF THE INVENTION

In biochemical analysis, by way of example, there is a high demand for arrangements and methods by means of which, using biochemical or biological or synthetic identification elements immobilized on a surface, one or a plurality of analytes in a supplied sample are to be detected with high selectivity and sensitivity. In this case, many known detection methods are based on the determination of one or a plurality of luminescences in the presence of the one or the plurality of analytes.

In this case, the term "luminescence" in this application denotes the spontaneous emission of photons in the ultraviolet to infrared range after optical or non-optical, such as, for example, electrical or chemical or biochemical or thermal excitation. By way of example, chemiluminescence, bioluminescence, electroluminescence and, in particular, fluorescence and phosphorescence are also encompassed by the term "luminescence".

The term "optical transparency of a material" is used hereinafter in the sense of requiring the transparency of this material at at least one excitation wavelength. At a longer or shorter wavelength, this material may also be absorbent.

By means of thin-film waveguides having a high refractive index, based on a thin wave-guiding film only a few hundred nanometers thick on a transparent carrier material, it has been possible in recent years to significantly increase the sensitivity for an analyte detection. This exploits the fact that the guiding of light in the material of a waveguide that has a high refractive index is associated with the formation of a so-called evanescent field which has a penetration depth of a molecular order of magnitude, that is to say of a few hundred nanometers, into the adjacent media having a lower refractive index. A strictly surface-bound excitation field is thus available which permits processes to be studied selectively within a layer thickness defined by the penetration depth of the evanescent field into the media having a low refractive index. By way of example, WO 95/33197 describes a method in which the excitation light is coupled into the wave-guiding film of a sensor platform via a relief grating as diffractive optical element. The surface of the sensor platform is brought into contact with a sample containing the analyte, and the isotropically emitted luminescence of substances capable of luminescence that are situated at the penetration depth of the evanescent field is measured by means of suitable measuring devices such as, for example, photodiodes, photomultipliers or CCD cameras. It is also possible for that portion of the radiation generated in evanescent fashion which is fed back into the waveguide to be coupled out and measured via a diffractive optical element, for example a grating. This method is described for example in WO 95/33198.

The terms "evanescent field" and "near field" are used synonymously below.

One disadvantage of the method for detecting luminescence excited in evanescent fashion as described previously in the prior art, in particular in WO 95/33197 and WO 95/33198, is that in each case only one sample is analyzed by means of the embodiments of sensor platforms described therein. In order to be able to carry out further measurements on the same sensor platform, complicated washing or cleaning steps are continuously required. This holds true particularly if an analyte that is different from the first measurement is intended to be detected. In the case of an immunoassay, this generally means that the entire immobilized layer on the sensor platform has to be exchanged or equally a new sensor platform as a whole has to be used.

For simultaneously or successively carrying out luminescence-based multiple measurements with essentially monomodal, planar inorganic waveguides, WO 96/35940, for example, has disclosed devices (arrays) in which at least two separate wave-guiding regions that are irradiated separately with excitation light are arranged on a sensor platform. However, dividing the sensor platform into separate wave-guiding regions disadvantageously has the consequence that the space requirement for discrete measurement regions, in discrete wave-guiding regions on the common sensor platform is relatively large and, therefore, it is again possible to achieve only a comparatively low density of different measurement zones (or so-called "features").

Therefore, there was a need to increase the feature density or to reduce the area required per measurement region.

Based on simple glass or microscope laminae, without additional wave-guiding layers, arrays are known in the form of so-called "microarrays" with a very high feature density. By way of example, U.S. Pat. No. 5,445,934 (Affymax Technologies) describes and claims arrays of oligonucleotides having a density of more than 1000 features per square centimeter for the detection of nucleic acids with complementary (partial) sequences. The excitation and the read-out of such arrays are based on traditional optical arrangements and methods. The entire array can be illuminated simultaneously with an expanded excitation light bundle, but this leads to a relatively low sensitivity since the excitation is not restricted to the interacting surface and since, moreover, the scattered light portion is relatively large and scattered light or background fluorescent light from the glass substrate is also generated in the regions in which there are no oligonucleotides immobilized for the binding of the analyte. In order to increase the excitation intensity and to improve the sensitivity during detection, frequently confocal measuring arrangements are used and the different features are read out sequentially by means of "scanning". However, this results in a longer expenditure of time for the read-out of a large array and a relatively complex optical construction.

Recently it was possible to show that the format of such "microarrays" can be applied to planar thin-film waveguides as carriers (sensor platform) without the portion of the luminescence which is excited in the evanescent field and is fed back into the waveguide leading to a significant crosstalk of signals from different measurement regions. With this arrangement it was possible to achieve a significant increase in the sensitivity, by a factor of 50 to 100, in comparison with the conventional measuring arrangements [G. L. Duveneck et al. Analytica Chemica Acta 469 (2002) 49-61].

For all of the configurations mentioned, however, ultimately primarily the background signals and the associated background noise remain limiting factors for the detection limits that can respectively be achieved. This is caused for these as well as for all the abovementioned excitation and detection configurations inter alia by the fact that in the case of most of the luminescent dyes used, the spectral distance between excitation and emission wavelengths (Stokes Shift) is relatively small, typically between 20 nm and 50 nm. Although some luminescent dyes are known which have a large Stokes Shift, up to approximately 300 nm, such as some lanthanide complexes, for example, these disadvantageously generally have a relatively low quantum efficiency and/or low photostability.

Moreover, in the case of the known arrangements based on thin-film waveguides having a high refractive index, for example based on wave-guiding layers made of $Ta_2O_5$ or $TiO_2$, with conventional excitation, it is disadvantageous that the propagation losses of these waveguides and also the intrinsic fluorescence of these thin-film waveguides (for example through traces of fluorescent contaminants in the carrier layer (b)), rise drastically at short excitation wavelengths. Thus, short-wave excitation is limited here at approximately 450 nm to 500 nm. An arrangement would be desirable, however, by means of which fluorophores can be excited even at shorter wavelengths and their luminescences can be detected with a lowest possible or at best even without any background.

Methods based on multiphoton excitation, in particular two-photon excitation, have been known for some years. However, a two-photon excitation requires extremely high field strengths or intensities of the excitation light. These are achieved in the arrangements described by means of powerful pulsed lasers having extremely short pulse lengths (typically of femtoseconds). Previous systems use optical arrangements which are associated with very high system costs and make high requirements of the technical qualification of the user. Therefore, they are not suitable for more routine applications, outside the area of research. The required intensity densities have previously been achieved for example by means of pulsed high-power lasers in confocal microscopic arrangements, as is described for example in U.S. Pat. No. 5,034,613, with a laser focus diameter of less than 1 micrometer in the focal plane of the microscope. However, measuring an extended area by means of scanning again disadvantageously also requires a high expenditure of time besides the high outlay on instrumentation.

It was recently shown that with the aid of planar thin-film waveguides it is possible to carry out two-photon luminescence excitation not only in a microscopic excitation beam diameter, but microscopically on areas of several square millimeters at the surface of a suitable thin-film waveguide [Duveneck, G. L., et al. "Evanescent-field-induced two-photon fluorescence: excitation of macroscopic areas of planar waveguides; Applied Physics B, 73 (2001) 869-871; WO 01/79821; WO 02/79765]. This novel combination of waveguide technology with two-photon luminescence excitation makes it possible for the long-wave excitation light to be spectrally distinctly separated from the shorter-wave emission light. However, this advantage of the greater spectral separation is partly canceled out again by virtue of the fact that, on account of the significantly lower quantum efficiencies of the two-photon-induced luminescence, in comparison with the conventional one-photon-induced luminescence, the ratio between only very weak emission intensity and very strong intensity of the excitation scattered light is significantly less favorable than in the case of the one-photon-induced luminescence.

Therefore, there is a need for a method and an analytical measuring arrangement by means of which an effective separation from the excitation light (excitation signal) can also be carried out for the two-photon-induced luminescence, as an example of optical signals which follow the intensity of an excitation signal in a nonlinear manner. At the same time it is desirable to advantageously utilize the specific property of the nonlinear correlation with the excitation light for such a method and such a measuring arrangement.

Spectral separation methods have the general disadvantage of never completely suppressing the excitation light (excitation signal) to be discriminated and of likewise incomplete transmission for the emission wavelength to be detected. In addition, by way of example, the effectiveness of interference filters is disadvantageously also significantly dependent on the angle at which the light impinges on the filter.

An elegant alternative to the spectral separation of excitation and emission signals consists in the so-called "lock-in" technique, which has already been known for a long time for point-type signal detection (that is to say in combination with zero-dimensional detectors) [Meade, M. L., "Lock-in amplifiers: principles and applications", London (1983), Peregrinus 232]. The basic principle of this technique is based on the modulation of the excitation signal with a selectable modulation frequency and the detection of the emission signal in a manner correlated with this modulation frequency. By way of example, the modulation of the excitation light intensity impinging on an interaction volume or on an interaction layer may be effected with the aid of a rotating disk with an arrangement of slits and closed regions (a so-called "chopper"), whereby the excitation light path is alternately blocked and released. As an alternative, it is also possible, for example, to modulate the excitation current of a laser diode. The resulting emission light under the periodically varying illumination conditions (in the absence and presence of excitation light) is directed onto a detector whose response time corresponds at least to the modulation frequency. An associated so-called lock-in amplifier amplifies only those signals which are correlated with the modulation frequency, by forming the difference between the detector signals forwarded to it at the different phases. The light portions measured by the detector which are not correlated with the modulated excitation intensity are thus eliminated. Under suitable conditions, the lock-in technique also makes it possible, by measuring the phase difference between maximum excitation light intensity and maximum emission light intensity, to determine the decay time, that is to say the life time of this emission after pulsed excitation.

In the case of the traditional lock-in technique described above, typically the signal portions which are proportional to the excitation light are selected for further processing by means of an individual detector ("point detector") and response signal portions which are not correlated with the excitation signal are rejected.

Various work on applying the lock-in technique described or methods related thereto to one- or two-dimensional detector arrays is known. WO 96/15625 describes a device and a method for detecting an intensity-modulated radiation field, the demodulation process being integrated electronically in a detector array. This method is suitable for example for propagation time measurements ("time of flight", TOF) or heterodyne interference measurements of remote moving objects. The method is based on the filtering of linear signal portions from the background light. The distance from an object, for example, is determined from the measured propagation time or phase shift in an interferometric method. It is mentioned in the description that, in the case of a sinusoidally modulated radiation field, for a number of four samplings (signal measurements) per period it is possible to determine the amplitude, the phase and the background light of the radiation field, and that when the sampling rate is increased, it is possible to determine further parameters of the radiation field, such as, for example, Fourier coefficients. However, no statements whatsoever are made with regard to how such a further development could be realized, rather exclusively the detection of linear signal portions of the radiation field is described. A publication [T. Spirig, P. Seitz, O. Vietze and F. Heitger, "The Lock-In CCD—Two-Dimensional Synchronous Detection of Light", IEEE Journal of Quantum Electronics 31 (1995) 1705-1708] of the underlying work describes the technical implementation of the detector in greater detail, where it is referred to as a "Lock-In CDD" (CCD: "Charge-coupled device"). Further developments of this arrangement are described in T. Spirig, M. Marley and P. Seitz, "The Multitap Lock-In CCD with Offset Subtraction", IEEE Transactions on Electronic Devices 44 (1997) 1643-1647 and in the International patent application WO 01/84182. However, neither work contains any indications whatsoever about possibilities for detecting signal portions correlated nonlinearly with the intensity of an excitation field available at the measurement location.

By contrast, the present invention relates to the separation of the nonlinear signal portions from the remaining portions which are linearly correlated or uncorrelated with a modulated excitation field. Following the present invention, then, the intention is for precisely those signal portions to be rejected whose detection is the object of the invention described in WO 96/15626 and the further publications mentioned above. Moreover, the arrangement according to the invention and the method according to the invention which is to be performed therewith have the advantage that they permit the use of any desired one- or two-dimensional detector array, provided that the electronic response time thereof is short enough to follow the frequency of the modulation of the excitation light power and thus the modulation of the intensity of the light that is to be detected and emerges from the measurement location. The use of detectors such as the "Lock-In CCDs" described is possible, but in no way necessary, for the arrangement according to the invention and the measuring method according to the invention.

The application of two-dimensionally spatially resolved phase-sensitive detection in interference microscopy was recently disclosed [A. Dubois, "Phase-map measurements by interferometry with sinusoidal phase modulation and four integrating buckets", J. Opt. Soc. Am. A 18 (2001) 1972-1979; A. Dubois, L. Vabre, A. C. Boccara and E. Beaurepaire, "High-resolution full-field optical coherence tomography with a Linnik microscope", Applied Optics 41 (2002) 805-812]. The arrangements described in each case use a commercial CCD camera as detector. As in an exemplary embodiment of our invention, the camera images are transmitted as data to a computer, and the phase-sensitive demodulation of these data is carried out by numerical analysis with the aid of the computer. The method described in the two publications mentioned is restricted to the separation of constant background light and linear interference signals which are generated by illumination with a light source. In the arrangements described, two light beams having a constant intensity but a modulated phase shift are caused to interfere. The measurement of two-dimensional height profiles, e.g. of surfaces with a patterning of the order of magnitude of micrometers or nanometers, is described as an application of this method. The mathematical method of the Fourier series expansion of a time signal is used in the two publications; only the phase angle of the first harmonic coefficient, which is a measure of the distance between the sample point (measurement location) and the detector, is explicitly used.

By contrast, the present invention does not relate to the measurement of height profiles, distance measurements, or object identification in the case of modulated illumination. Under the conditions of the application of our invention, the position of the measurement location is known very precisely. Moreover, the present invention does not require generation of interference patterns, but is suitable for analyzing these, too, provided that they have nonlinear signal portions. In contrast to the determination—described in the two publications—of signal portions that are correlated linearly with an excitation light from a previously unknown measurement location that is to be determined by this analysis, the present invention is provided for the generation—spatially resolved into one or more spatial coordinates—of images of signals that are correlated nonlinearly with an excitation light and emerge from a well-known measurement location. One possible embodiment of the invention is based on phase-sensitive detection at the second harmonic of the excitation modulation. In this case, the phase angle of the nonlinear signal does not supply any information about the spatial position, but rather about the chemical character, for example. It is thus possible to measure e.g. excitation lifetimes, in contrast to propagation time differences in the case of the publications cited above.

DETAILED DESCRIPTION OF THE INVENTION

It has now been found, surprisingly, that with an analytical system according to the invention and an analysis method performed therewith it is possible to unequivocally detect optical signals that are correlated nonlinearly with a modulated excitation signal without additional filtering, such as spectral filtering, for example, even though they are in no way identifiable in the originally recorded signal against the signal noise associated therewith. This is made possible according to the invention by not only exclusively selecting the signal portions that are correlated nonlinearly with the excitation light and rejecting the remaining signal portions, but at the same time significantly reducing the noise of the selected nonlinear signal in comparison with the noise of the original signal.

A first subject matter of the present invention is a method for the highly sensitive simultaneous measurement of nonlinear optical emission signals, spatially resolved in one or two spatial dimensions, comprising:

radiating the excitation light from at least one light source in a power-modulated and/or pulse-duration-modulated form into an interaction volume or to an interaction area or an interaction layer (referred to jointly by the designation "interaction spaces"), in each of which interaction spaces one or a plurality of emissions that are correlated nonlinearly with the excitation light can be excited, measuring the light emerging from said interaction spaces by means of a one- or two-dimensional detector array, transmitting the measurement data from said detector array to a computer and formatting the data in a one- or multidimensional data matrix, characterized in that those portions of the light emerging from the interaction spaces which are linearly proportional to the intensity of the excitation light available in the interaction spaces are separated from portions of the light emerging from the interaction spaces which are nonlinearly proportional to the available excitation light intensity.

In this case, an "interaction volume" is to be understood as a three-dimensional volume upon which the excitation light acts and in which, under suitable conditions, it is possible to generate response signals that are correlated nonlinearly with the intensity of an excitation light radiated in in modulated fashion. By way of example, said nonlinearly correlated response signals may be a luminescence after multiphoton excitation or a "second harmonic" signal, that is to say a response signal at half the excitation wavelength radiated in (frequency-doubled signal). Such signals may emerge for example from suitable chromophores. Multiphoton-induced emissions can be generated in the case of a multiplicity of chromophores provided that sufficiently high excitation intensities are provided. For the excitation of luminescence (more precisely fluorescence) after two-photon absorption, rhodamines are known as being particularly well suited. For "second harmonic generation", molecules having an asymmetrical arrangement of their molecular groups are known as being particularly suitable.

Accordingly, an "interaction area" is to be understood as the surface between a fixed carrier and an adjacent medium or the interface between different physicochemical phases (which may e.g. also be different liquids that are immiscible) at which or on which it is possible to generate response signals that are correlated nonlinearly with the excitation light.

An "interaction layer" is intended to be a layer above or below such an interaction area in which the nonlinear response signals can be generated. By way of example, such an "interaction layer" may be the volume of a medium above an optical waveguide, the layer thickness being defined by the penetration depth of the evanescent field of the light guided in the waveguide or in the wave-guiding layer or the wave-guiding film into said medium.

The terms "interaction volume", "interaction area" and "interaction layer" thus defined are intended to be referred to jointly by the designation "interaction space".

"Response signals that are correlated nonlinearly with an excitation light or the intensity thereof" are intended to denote those signals which exhibit a strictly monotonic change with the magnitude (intensity) of the excitation signal, which, however, is not of a linearly proportional nature. Signals which, in the event of a change in the excitation light or the intensity thereof, change in a non-systematic manner or in a purely statistical way are intended to be designated as being "uncorrelated" with the excitation light or with the intensity thereof.

"Power-modulated form" and "pulse-duration-modulated form" are intended to be designated in summary as "modulated form" of the excitation light.

The modulation of the excitation light may be effected in various ways. By way of example, this may be effected with the aid of an acousto-optical modulator (AOM), a liquid crystal (LCD) attenuator, a rotating wave plate in combination with a polarizer or a variable neutral density filter.

The separation of the different signal portions that are correlated with the excitation light intensity is effected from the processing of the response signals that are recorded at different excitation powers and are spatially resolved into one or two spatial dimensions. This may involve for example images which are recorded by means of a CCD camera and are transmitted in digital form to a computer and are correspondingly stored in a one- or multidimensional data matrix.

One preferred embodiment of the method according to the invention is characterized in that it does not comprise any spectral filtering of the light that is to be detected and emerges from the interaction spaces. However, the method according to the invention may also be carried out in combination with such a spectral filtering. In this case, it is preferred to use such spectrally selectively optical components which acquire an existing spatial resolution of the signals (such as, for example, two-dimensional measurements of light intensities). By way of example, cut-off filters (e.g. high-pass or low-pass filters) and bandpass filters (such as e.g. interference filters, Nodge filters, etc.) are suitable.

Said one- or two-dimensional detector array may be selected from the group comprising CCD cameras, CCD chips, CMOS cameras, CMOS chips, photodiode arrays, avalanche diode arrays, multichannel plates and multichannel photomultipliers, it being possible for a phase-sensitive demodulation to be integrated into said detector array. The temporal resolution of the detection should be high enough that it can follow at least double the frequency of the modulation of the excitation light. In this case, it proves to be a further important advantage of the present invention that it is even possible to use detectors with relatively strong noise which are relatively inexpensive but could not be used hitherto for highly sensitive measurements on account of the high noise, since the noise components that are uncorrelated with the excitation light are eliminated according to the invention.

A multiplicity of possible embodiments of the method according to the invention are distinguished by the fact that the modulation of the excitation light radiated in to an interaction space is effected by means of optomechanical and/or acousto-optical and/or electro-optically active auxiliary means.

Said optomechanical and/or acousto-optical and/or electro-optically active auxiliary means may be selected from the group comprising mechanical shutters (comparable to camera shutters) and rotating choppers which in each case alternately block and release the light path between the excitation light source and the interaction space, polarization-selective components such as, for example, rotating half-wave plates in combination with polarizers, liquid crystal attenuators, electro-optically active crystals, neutral density filters that are locally or temporally variable in terms of their transmission, acousto-optical modulators and also modulators based on interference effects, such as, for example, Michelson interferometers or Mach-cylinder interferometers.

What is characteristic of other embodiments of the method according to the invention is that the modulation of the excitation light radiated in to an interaction space is effected by means of direct, active modulation of the light radiated from the excitation light source. By way of example, it is possible for the modulation of the excitation light radiated in to an interaction space to be effected by means of modulation of the excitation current for a semiconductor laser as excitation light source.

Numerous possible embodiments of the method according to the invention are distinguished by the fact that the modulation of the excitation light radiated in to an interaction space is effected periodically. However, it is also possible for the modulation of the excitation light radiated in to an interaction space to be effected non-periodically.

A majority of the possible embodiments of the method according to the invention are distinguished by the fact that the modulation of the excitation light radiated in to an interaction space consists in the modulation of the intensity radiated in.

One special variant consists in the fact that the modulation of the excitation light radiated in to an interaction space consists in the simultaneous modulation of the pulse duration and the peak power of the excitation light radiated in, the peak power preferably being varied inversely proportionally to the pulse duration and the integral of the pulse power particularly preferably remaining constant.

It is possible to carry out the method according to the invention without detection of the modulated excitation light or a measurement variable proportional thereto. Preference is given, however, to those embodiments of the method which comprise in addition to the detection of the light emerging from the interaction spaces, the detection of the modulated excitation light or a measurement variable proportional thereto.

In the context of the method according to the invention, the detection of the light emerging from the interaction spaces is typically effected in a manner temporally correlated with the modulation of the excitation light power. In this case, it is possible for the detection of the light emerging from the interaction spaces to be effected with a frequency corresponding to an integer multiple of the modulation frequency of the excitation light power.

In accordance with the present method according to the invention, various embodiments are possible for carrying out the separation of the response signal portions that are correlated differently with the excitation light intensity.

A plurality of possible embodiments are distinguished by the fact that the separation of the response signal portions from the interaction space that are correlated nonlinearly with the excitation light power from the remaining signal portions is effected with the aid of a parallel series expansion. It is preferred for the separation of the response signal portions from the interaction space that are correlated nonlinearly with the excitation light power from the remaining signal portions to be effected with the aid of a parallel Taylor expansion. The procedure is described in detail in example 3.1, in the section concerning the exemplary embodiments of the invention.

Other preferred embodiments of the method according to the invention are distinguished by the fact that the separation of the response signal portions from the interaction space that are correlated nonlinearly with the excitation light power from the remaining signal portions is effected with the aid of a harmonic analysis. The harmonic analysis is based on the fact that nonlinear systems generate harmonics in the case of harmonic excitation (modulation at a constant frequency). The parameters of said harmonics can be determined by Fourier analysis. Signals that are correlated linearly with the excitation light, for example from scattered light, do not contribute to higher harmonics. Further explanations in this respect are given in example 3.2. With the aid of this embodiment of the method according to the invention, it is possible, for example, upon detection of the second harmonic, to produce scattered-light-free images of luminescence signals induced by two-photon absorption.

What is characteristic of a further preferred group of embodiments is that the separation of the response signal portions from the interaction space that are correlated nonlinearly with the excitation light power from the remaining signal portions is effected by means of a stepped modulation of the excitation light power.

It is particularly preferred for the separation of the response signal portions from the interaction space that are correlated nonlinearly with the excitation light power from the remaining signal portions to be effected using a four-step algorithm for the modulation of the excitation light power. This variant is distinguished by the fact that it can be implemented particularly simply in practice. In this embodiment of the method according to the invention, the power of the excitation light is not modulated continuously at one frequency, but rather is set periodically in steps to four discrete values. This advantageously has the effect that the outlay for carrying out the required calculations can be significantly reduced in comparison with other variants. This embodiment is described in detail in example 3.3.

For the abovementioned embodiments with a stepped modulation of the excitation light power, the step sizes are advantageously chosen such that the portions that are uncorrelated with the excitation light or the portions that are correlated linearly with the excitation light and are to be eliminated in the mathematical analysis step of the method according to the invention can be summed to zero in each case in a computationally simple manner. In experimental practice, however, the excitation light powers often cannot be set exactly to the desired values required therefor, for example because the measurement of the excitation light power arriving in the interaction space is difficult to carry out.

Therefore, a further preferred embodiment is distinguished by the fact that experimentally dictated deviations of the excitation light powers from the desired values provided for the modulation are compensated for by means of numerical corrections. In particular, it is advantageous, if necessary, if the response signals measured using a four-step algorithm for the modulation are multiplied by correction factors. The procedure for determining correction factors is described in example 3.3.1.

It is advantageous if it is possible to determine the correction factors for the response signals from measured excitation light powers for the generation of said response signals. However, such a measurement often cannot be carried out at least with the required accuracy. It is then preferred for the correction factors for the response signals to be determined by a numerical analysis of the response signal data generated, it being possible for this to be effected for example by evaluation of the signals from partial regions—identified for this—of an interaction space or with the aid of separate measurements (for example using a calibration sample).

The calculations associated with the method according to the invention can be carried out in a very short time by means of commercially available computers. Therefore, the method according to the invention is distinguished by the fact that the separation of the response signal portions from the interaction space that are correlated nonlinearly with the excitation light power from the remaining signal portions is effected in real time contemporaneously (within the recording time for the signal recording) with the recording of the signals from the interaction space.

It is preferred for the interaction space to be an interaction layer at a surface of a fixed carrier, the areal extent of the interaction space (on said surface of this carrier) being defined by the interaction area with the impinging power-modulated excitation light and its depth (extent perpendicular to said surface of the carrier) being defined by the range of the modulated excitation light intensity in this space dimension perpendicular to said surface of the carrier. The conditions are typically selected such that the excitation light intensity has a maximum value of specific magnitude at said surface and decreases with distance from the fixed carrier and said surface. By way of example, a distance from said surface at which the excitation light intensity has decreased to 1/e multiplied by the intensity at said surface can then be designated as the range of the excitation light intensity.

It is additionally preferred for there to be situated within the interaction space compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated.

The method according to the invention may advantageously be used in biochemical analysis. A multiplicity of biochemical analytical methods are based on the fact that the detection of one or a plurality of analytes is based on the specific binding thereof to immobilized specific binding partners.

Therefore, preferred embodiments of the method according to the invention are characterized in that there are immobilized on the surface of said fixed carrier one or a plurality of specific binding partners for the detection of one or a plurality of analytes in a binding assay (with the binding partner from a supplied solution binding to the immobilized binding partner), the analyte detection being effected on the basis of an optical response signal—correlated nonlinearly with the excitation light power—of the immobilized binding partner itself or of the binding partner supplied in solution or of one or a plurality of further binding partners supplied in one or a plurality of additional method steps.

In this case, one possible variant is characterized in that the specific binding partners immobilized on the surface of said fixed carrier are the one or the plurality of analytes themselves which are immobilized in a manner embedded in a native sample matrix or in a form of the sample matrix that is modified by means of one or a plurality of conditioning steps.

The native sample matrix or sample matrix modified in one or a plurality of conditioning steps may be selected for example from the group of extracts of healthy or pathological cells (e.g. of human, animal, bacterial or vegetable cell extracts), extracts of animal or human tissue, such as, for example, organ, skin, hair or bone tissue, or of plant tissue, and also of bodily fluids or constituents thereof, such as, for example, blood, serum or plasma, synovial fluids, lachrymal fluid, urine, saliva, tissue fluid, lymph. In particular, extracts of stimulated or untreated cells and extracts of healthy or pathological tissue may also be involved. The sample may be taken for example from an organism or tissue or cell assemblage or cell by means of a method from the group of tissue sections, biopsy and "laser capture microdissection".

Another variant of the method according to the invention using immobilized specific binding partners consists in the fact that the specific binding partners immobilized on the surface of said fixed carrier are biological or biochemical or synthetic identification elements for the specific identification of one or a plurality of analytes situated in a supplied sample.

Said binding partners, that is to say the analytes to be detected that are themselves immobilized or the analytes to be detected in a supplied sample and/or their biological or biochemical or synthetic identification elements that are immobilized or supplied in a supplied detection reagent, may be selected for example from the group comprising proteins, for example monoclonal, or polyclonal antibodies and antibody fragments, peptides, enzymes, glycopeptides, oligosaccharides, lectins, antigens for antibodies, proteins functionalized with additional binding sites ("tag proteins", such as, for example, "histidine tag proteins"), and also nucleic acids (for example DNA, RNA, oligonucleotides) and nucleic acid analogs (e.g. PNA), aptamers, membrane-bound and isolated receptors and ligands thereof, cavities produced by chemical synthesis for receiving molecular imprints, natural and synthetic polymers, etc.

It is preferred for on the surface of said fixed carrier, applied compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated, or applied specific binding partners to be immobilized in discrete measurement regions (spots) which may have an arbitrary geometry, for example circular, oval, triangular, rectangular, polygonal form, etc., it being possible for an individual measurement region to contain identical or different compounds or substances or molecular subgroups or specific binding partners.

Said discrete measurement regions are produced by spatially selective application of compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated, or by application of specific binding partners on said fixed carrier, preferably using one or a plurality of methods from the group of methods comprising "inkjet spotting", mechanical spotting, "microcontact printing", fluidic contacting of the regions for the measurement regions to be created with the compounds to be immobilized by supplying the latter in parallel or crossed microchannels, under the action of pressure differences or electrical or electromagnetic potentials, and also photochemical and photolithographic immobilization methods.

In many cases, the detection limit of an analytical method is limited by signals on account of so-called nonspecific binding, that is to say by signals which are generated by binding of analytes or other compounds which are used for the detection of said analytes and which are bound to the surface of the fixed carrier not only in the region of the immobilized specific binding partners but also in regions not covered by the latter, for example by hydrophobic absorption or by electrostatic interactions. Therefore, it is advantageous if there are applied between the spatially separate measurement regions or in unoccupied partial regions within said measurement regions compounds that are "chemically neutral" with respect to the analytes and/or with respect to its binding partners, preferably for example comprising the groups comprising albumins, in particular calf serum albumin or human serum albumin, casein, nonspecific, polyclonal or monoclonal antibodies, heterologous antibodies or antibodies that are empirically nonspecific to the analyte or analytes to be detected and the binding partners thereof (in particular for immunoassays), detergents—such as, for example, Tween 20—, fragmented natural or synthetic DNA that does not hybridize with polynucleouides to be analyzed, such as, for example, extracts of herring or salmon sperm (in particular for polynucleotide hybridization assays), or else uncharged but hydrophilic polymers, such as, for example, polyethylene glycols or dextrans.

A multiplicity of methods are known for the immobilization of molecules or molecular groups or complexes on a fixed carrier. One possibility consists in the fact that at the surface of said fixed carrier, applied compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated, or applied specific binding partners are immobilized directly or by means of a so-called spacer (formed as an independent molecule or molecular group) at the surface of said fixed carrier, with utilization of one or a plurality of types of interactions from the group of interactions comprising hydrophilic interactions, electrostatic interactions and covalent binding.

In general, however, it is advantageous if an adhesion promoting layer is applied between the surface of said fixed carrier and the immobilized compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated, or the applied specific binding partners, which adhesion promoting layer preferably has a thickness of less than 200 nm, particularly preferably of less than 20 nm, and preferably comprises a chemical compound from the groups comprising silanes, functionalized silanes, epoxides, functionalized, charged or polar polymers and "self-assembled passive or functionalized monolayers or multilayers", thiols, alkyl phosphates and phosphonates, multifunctional block copolymers, such as, for example, poly (L)lysine/polyethylene glycols.

A multiplicity of discrete measurement regions with identical or different specific binding partners contained therein may be arranged on the surface of the fixed carrier. In this case, more than 10, preferably more than 100, particularly preferably more than 1000 measurement regions may be arranged on a square centimeter in a two-dimensional arrangement.

It is preferred for said fixed carrier to be optically transparent at the wavelength of the acting excitation light. Moreover, it is advantageous if said fixed carrier is essentially planar.

Furthermore, it is preferred for said fixed carrier to comprise an optical waveguide structure, comprising one or a plurality of layers.

Therefore, it is particularly preferred for said fixed carrier to comprise a planar optical waveguide that is continuous or divided into discrete wave-guiding regions, comprising one or a plurality of layers.

It is especially preferred for said fixed carrier to comprise a planar optical thin-film waveguide with an essentially optically transparent, wave-guiding layer (a) on a second, likewise essentially optically transparent layer (b) having a lower refractive index than layer (a) and, if appropriate, a likewise essentially optically transparent intermediate layer (b') between layer (a) and layer (b) likewise having a lower refractive index than layer (a).

There are a series of different technical solutions for coupling excitation light into an optical waveguide. It is preferred for a wave-guiding layer of said fixed carrier to be in optical contact with one or a plurality of optical coupling elements which enable excitation light to be coupled into said waveguiding layer, said optical coupling elements being selected from the group of prism couplers, evanescent couplers with united optical waveguides with overlapping evanescent fields, end face couplers with focusing lenses, preferably cylindrical lenses, arranged before an end side of said waveguiding layer of the evanescent field sensor platform, and grating couplers.

It is particularly preferred for one or a plurality of grating structures (c) which enable excitation light to be coupled in to be fashioned in a wave-guiding layer of the fixed carrier.

In addition, it is advantageous if one or a plurality of grating structures (c') having an identical or different grating period and grating depth with respect to grating structures (c) are fashioned in a wave-guiding layer of the fixed carrier and enable light guided in said wave-guiding layer to be coupled out.

Various embodiments of optical waveguide structures, in particular based on thin-film waveguides, and also of optical systems which are suitable for the method according to the invention and also as part of an analytical system according to the invention as described below have been described for example in the International patent applications WO 95/33197, WO 95/33198, WO 96/35940, WO 98/22799, WO 99/58963, WO 01/13096, WO 01/43875, WO 01/55691, WO 01/79821, WO 01/92870, WO 02/20873, WO 02/21110, WO 02/40998, WO 02/46756 and WO 02/79765. The entire scope of the content of these applications is hereby incorporated as part of the present invention.

The signals that are correlated nonlinearly with the excitation light and are to be detected by means of the method according to the invention may be of varying nature. By way of example, one possibility is for said optical emission signals that are correlated nonlinearly with the excitation light intensity to comprise the signals of a frequency doubling ("second harmonic generation"), summation or differential frequency generation.

It is preferred for said optical emission signals that are correlated nonlinearly with the excitation light intensity to be induced by a multi-photon absorption.

It is particularly preferred for said optical emission signals that are correlated nonlinearly with the excitation light intensity to be induced by a two-photon absorption.

A further subject matter of the present invention is an analytical system for the highly sensitive simultaneous measurement of nonlinear optical emission signals, spatially resolved in one or two spatial dimensions, comprising:
  at least one light source for emitting excitation light,
  technical auxiliary means for the power modulation and/or pulse duration modulation of the excitation light emerging from the at least one light source,
  an interaction volume or an interaction area or an interaction layer, designated jointly as "interaction space", wherein one or a plurality of emissions that are correlated nonlinearly with the excitation light can be excited,
  at least one one- or two-dimensional detector array for measuring the light emerging from the interaction space,
  a computer to which the measurement data of said detector arrays are transmitted and with the aid of which the measurement data are formatted in a one- or multidimensional data matrix and analyzed, characterized in that those portions of the light emerging from the interaction spaces which are linearly proportional to the intensity of the excitation light available in the interaction spaces are separated from portions of the light emerging from the interaction spaces which are nonlinearly proportional to the available excitation light intensity.

The same types of possible embodiments and preferences as for the method according to the invention described above exist for the analytical system according to the invention.

A further subject matter of the invention is the use of an analytical system according to the invention and/or of a method according to the invention for quantitative and/or qualitative analyses for determining chemical, biochemical or biological analytes in screening methods in pharmaceutical research, combinatorial chemistry, clinical and preclinical development, for real-time binding studies and for determining kinetic parameters in affinity screening and in research, for qualitative and quantitative analyte determinations, in particular for DNA and RNA analysis and the determination of genomic or proteomic differences in the genome, such as, for example, single nucleotide polymorphisms, for measuring protein-DNA interactions, for determining control mechanisms for mRNA expression and for protein (bio)synthesis, for drawing up toxicity studies and also for the determination of expression profiles, in particular for determining biological and chemical marker substances, such as mRNA, proteins, peptides or low molecular weight organic (messenger) substances, but also for detecting antibodies, antigens, pathogens or bacteria in pharmaceutical product research and development, human and veterinary diagnosis, agrochemical product research and development, symptomatic and presymptomatic plant diagnosis, for patient stratification in pharmaceutical product development and for therapeutic medicament selection, for detecting pathogens and harmful substances, in particular salmonellae, prions, viruses and bacteria, in particular in foodstuffs analysis and ecological analysis.

Part of the invention is, moreover, the use of an analytical system according to the invention and/or of a method according to the invention in nonlinear optics, material research, investigation of processes at phase boundaries and surfaces of solid bodies, quality control of optical components, in particular for laser technology, for example of frequency-doubling components.

The invention is explained in more detail below by way of example, that is to say without restricting the generality.

EXAMPLES

An analytical system according to the invention comprises an interaction space in accordance with the abovementioned definition, in which it is possible to generate response signals that are correlated nonlinearly with variations of an excitation light radiated in, an optical system for the excitation and detection (by means of a one- or two-dimensional detector array) of said response signals, a computer to which the detector signals are transmitted and stored in a data matrix and with the aid of which the measurement data are then split—according to a specification according to the invention—into their portions that are differently correlated with the excitation light.

A method according to the invention comprises the use of an analytical system according to the invention for generating and detecting response signals that are correlated nonlinearly with an excitation light in an interaction volume as defined above, and the splitting of the recorded measurement data according to their portions that are differently correlated with the excitation light.

The analytical system and method according to the invention are explained below by way of example on the basis of their constituent parts mentioned, predominantly for the special case of the detection of luminescence induced by two-photon excitation, but they can generally be applied to the detection and quantification of processes that are correlated nonlinearly with an excitation light.

1. Interaction Space for Generating Nonlinearly Correlated Optical Signals

What is used as an interaction space in the sense of the preceding definition, in which nonlinear optical signals are intended to be generated, is the layer which adjoins the surface of a planar thin-film waveguide and the lateral extent of which is defined by the propagation length and width of an excitation light guided in the waveguide and the height of which over the waveguide is defined by the penetration depth of the evanescent field above the waveguide.

Figure 1:
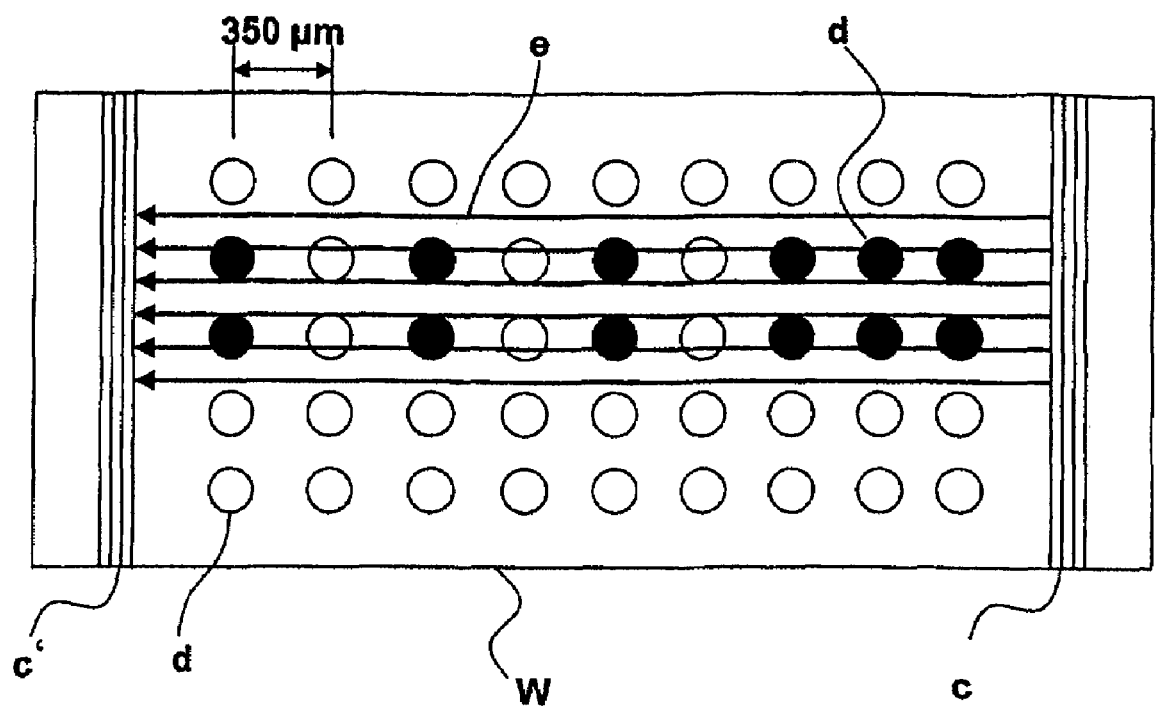
FIG. 1 shows, as an example of an interaction space for the generation of optical signals that are correlated nonlinearly with an excitation light, the schematic diagram of a thin-film waveguide in plan view, with gratings for coupling light into and out of the waveguide, between which gratings the light is guided in the waveguide, and with measurement regions produced on the surface in the form of circular regions of applied material (designated as a whole as "sensor platform"), in which the generation of response signals that are correlated nonlinearly with the excitation light is intended to be detected.

The waveguide structure (W)(FIG. 1) is formed by a thin wave-guiding film made of tantalum pentoxide (wave-guiding, optically transparent layer (a), n=2.092 at 800 nm) which has a thickness of 150 nm and is applied on a glass substrate (AF45 glass as optically transparent layer (b), n=1.496 at 800 nm) (layer structure not shown in FIG. 1). Coupling gratings (c, c') in the form of relief gratings (grating period 360 nm, grating depth 12 nm) produced with a spacing of 9 nm in the layer (a) serve for coupling light into and out of the wave-guiding layer (a). Under these conditions, for excitation light having a wavelength of 800 nm, the coupling-in angle from the glass substrate to the wave-guiding layer (a), relative to the normal to the plane of the surface of the waveguide structure, is −20.4°; the outer angle of incidence on the layer (b), in order to fulfill the coupling-in condition, is −31.4°.

On the waveguide structure, between a first coupling grating (c)(on the right in FIG. 1) serving for coupling in the excitation light and a second coupling grating (c')(on the left in FIG. 1) serving for coupling out the light guided in the wave-guiding film, different dyes capable of luminescence are applied in different concentrations in discrete measurement regions ("spots", spot diameter 120 μm, (center-to-center) spot distance 350 μm). (d) designates measurement regions produced by application of dyes to be investigated on the waveguide structure, circles that are filled in indicating measurement regions that are luminescent under the experimental conditions and circles that are not filled in indicating measurement regions that are not luminescent. Said dyes capable of luminescence are intended to be investigated with regard to their possibilities for emitting signals that are correlated nonlinearly with a modulated excitation light intensity. (e) indicates the trail of the excitation light guided in the layer (a).

Figure 2:
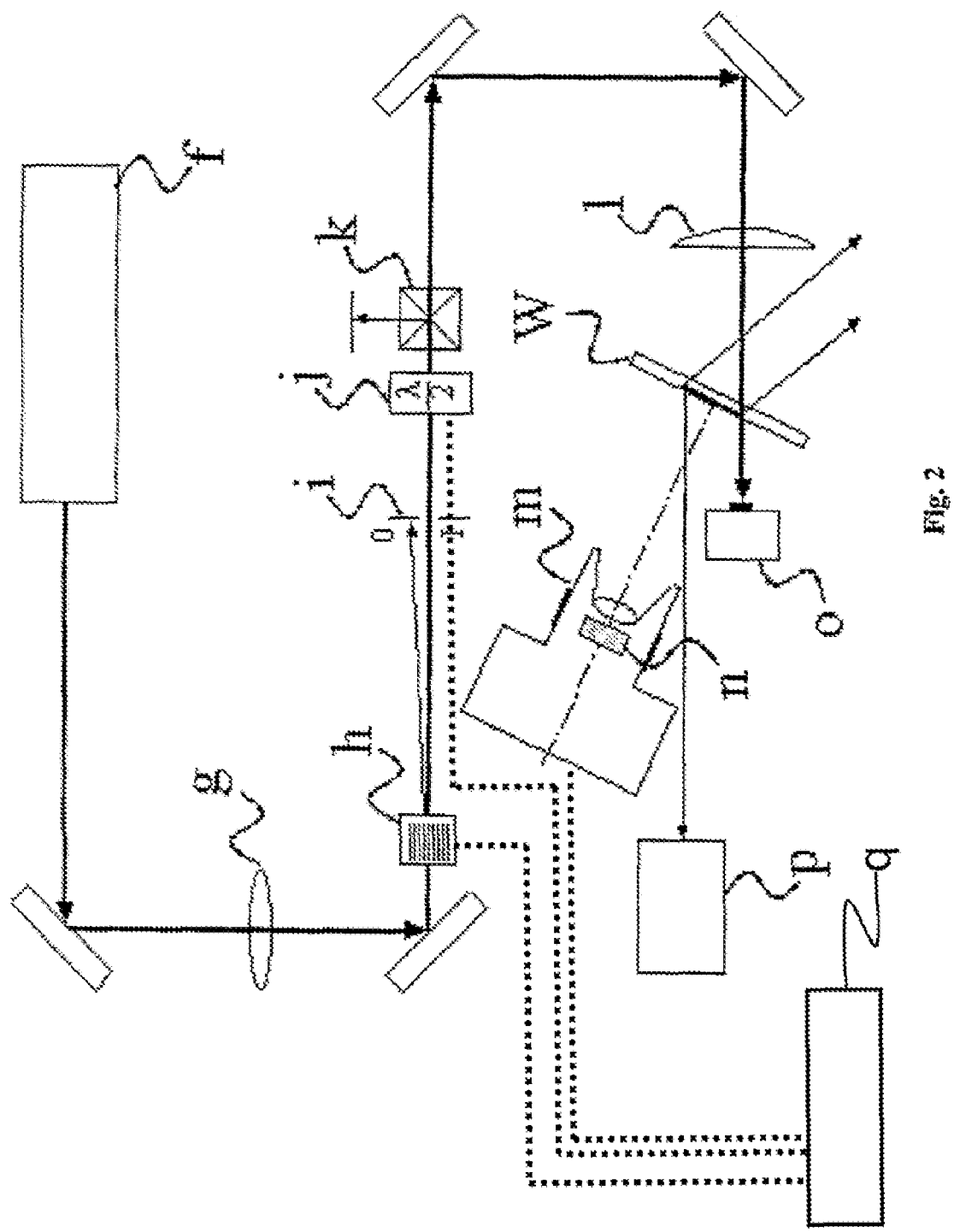
FIG. 2 shows a suitable optical system for generating signals that are correlated nonlinearly with the excitation light, as part of an analytical system according to the invention.

2. Optical System for Generating Signals that are Correlated Nonlinearly with the Excitation Light A suitable optical system for generating signals that are correlated nonlinearly with the excitation light, as part of an analytical system according to the invention, is illustrated in FIG. 2. What is used as an excitation light source (f) is a pulsed titanium-sapphire laser with emission at approximately 800 nm (pulse length: 100 fsec., repetition rate: 80 MHz, average power used: up to 1.5 W, spectral pulse width: 8 nm, Tsunami model 3960, Spectra Physics, Mt. View, Calif., USA). After the light has passed through a beam shaping optic (g), the intensity of the excitation light emitted by the laser can be regulated by means of an acousto-optical modulator (h)(fused silica crystal, 60 MHz carrier frequency, ASM-601-23, IntraAction, Bellwood, Ill., USA) continuously between 0% and 80% of the output power. In this case, an aperture (i) serves to mask out the zeroth order of the transmitted light downstream of the acousto-optical modulator. As an alternative, with the aid of a rotating half-wave plate (j) for 800 nm and a polarizer (k), it is possible to regulate the intensity of the excitation light between 0% and 100% of the output power. Both intensity regulations can be controlled by means of a computer (q).

Downstream of the components for intensity regulation that are to be used alternatively, lenses (l), e.g. cylindrical lenses, may be inserted in the excitation beam path (in the direction of the waveguide structure) in order to generate excitation light bundles of desired geometry that are radiated in in parallel fashion on the coupling-in grating (c) of the waveguide structure (W). The excitation light radiated in is deflected by means of a mirror onto the coupling-in grating (c) of the waveguide structure, which is mounted on an adjusting element permitting translation in the x, y and z directions (parallel and in the axes perpendicular to the grating lines) and rotation (with axis of rotation matching the grating lines of the coupling-in grating).

For the steps of the experiment reported below, the laser beam of the excitation light source is in most cases collimated by means of a cylindrical lens (f=40 nm) perpendicularly to the grating lines, so that an elliptically illuminated region of approximately 0.1 nm×1 mm to 2 mm (with the long axis parallel to the grating lines) is typically produced on the grating. The full width at half maximum of the excitation light coupled into the wave-guiding layer is typically correspondingly 1 mm to 2 mm under these conditions. In an earlier work (WO 02/79765) it was shown that under these conditions, along the entire trail of the light guided in the waveguide, at the waveguide surfaces, it is possible to generate luminescence excitation by two-photon absorption, as a special case of response signals that are correlated nonlinearly with an excitation light.

The intensity of the excitation light of the pulsed laser (pulse frequency: 80 MHz) that impinges on the coupling-in grating of the waveguide structure is sinusoidally modulated periodically by rotating of a half-wave plate (j) situated in the excitation beam path given a constant setting of a polarizer (k) that is likewise mounted in the excitation beam path. One complete rotation of the half-wave plate is associated with four complete, sinusoidal modulation periods of the excitation light intensity incident on the coupling-in grating. The light emerging from the waveguide structure is collected by means of a collecting optic and, without any further spectrally selective components in the emission beam path, is directed onto a CCD camera (m)(AstroCam, TE3/A, Cambridge, GB) as detector. During one revolution of the half-wave plate, about 100 camera images are recorded and their digital, pixel-resolved data are conducted to a computer for further processing.

As further optional optical components, FIG. 2 indicates an interference filter (n), which may be positioned before the CCD camera, an optical power measuring unit (o), which can be used for example to measure the intensity of the transmitted light portion downstream of the waveguide structure, and an optical spectrometer (p), which can be used for example to analyze the spectrum of the light coupled out at the second grating (c'). These last-mentioned components are not necessary constituent parts of an analytical system according to the invention.

3. Separation of the Signal Portions that are Differently Correlated with the Excitation Light Intensity For implementing the separation of the response signal portions that are differently correlated with the excitation light intensity, various embodiments are possible in accordance with the present analytical system according to the invention and the method according to the invention which is to be performed therewith.

3.1 Parallel Taylor Expansion

Let there be a response signal s as a function of the power p of an excitation light in the form of a Taylor series.

$$s = a_0 + a_1 \cdot P + a_2 \cdot P^2$$

$a_0$ background, $a_1$ linear scattered light, $a_2$ nonlinear signal.

If s(P) is measured for three different powers P, it is possible to calculate the values for $a_0$, $a_1$ and $a_2$. An image of $a_2$ for each pixel produces a background- and scattered-light-free image of the nonlinearly correlated signal portion (in the special case of the luminescence signal induced by two-photon absorption).

If s(P) is measured for more than three powers, then it is possible to determine the values for $a_0$, $a_1$ and $a_2$ according to a compensating calculation according to Gauss' least square error method. For the case of equation (1) this calculation produces a polynomial algorithm which can easily be vectorized. It is thus possible to calculate the coefficients $a_0$, $a_1$ and $a_2$ for an entire image within a very short time (in real time).

We choose the following designations:

$P^{(n)}$ ... incident power, image n $s_{(x,y)}^{(n)}$ ... signal of the pixel (x,y), image n $a_{k_{(x,y)}}$ ... $\alpha_0, \alpha_1, \alpha_2$ coefficient of the pixel (x,y)

Application of Gauss' principle to the equation (1) produces:

$$\frac{\partial}{\partial a_{k_{(x,y)}}} \sum_n \left( s_{(x,y)}^{(n)} - a_{0_{(x,y)}} - a_{1_{(x,y)}} P^{(n)} - a_{2_{(x,y)}} P^{(n)^2} \right)^2 = 0 \quad (2)$$

for $k = 0, 1, 2$ from which follows:

$$\begin{cases} a_{0_{(x,y)}} \sum_n 1 + a_{1_{(x,y)}} \sum_n P^{(n)} + a_{2_{(x,y)}} \sum_n P^{(n)^2} = \sum_n s_{(x,y)}^{(n)} \\ a_{0_{(x,y)}} \sum_n P^{(n)} + a_{1_{(x,y)}} \sum_n P^{(n)^2} + a_{2_{(x,y)}} \sum_n P^{(n)^3} = \sum_n P^{(n)} s_{(x,y)}^{(n)} \\ a_{0_{(x,y)}} \sum_n P^{(n)^2} + a_{1_{(x,y)}} \sum_n P^{(n)^3} + a_{2_{(x,y)}} \sum_n P^{(n)^4} = \sum_n P^{(n)^2} s_{(x,y)}^{(n)} \end{cases} \quad (3)$$

and using the following abbreviation $$Sp_0 = \sum_n 1 = N, \; Sp_1 = \sum_n P^{(n)}, \ldots, Sp_4 = \sum P^{(n)^4} \quad (4)$$

$$Sz_{(x,y)} = \sum_n s_{(x,y)}^{(n)}, \; Szp_{(x,y)} \quad (5)$$

$$= \sum_n s_{(x,y)}^{(n)} P^{(n)}, \; Szp_{2(x,y)}$$

$$= \sum_n s_{(x,y)}^{(n)} P^{(n)^2}$$

the following is produced as a solution $$L = \begin{pmatrix} a_{0_{(x,y)}} & a_{1_{(x,y)}} & a_{2_{(x,y)}} \end{pmatrix} \quad (6)$$

$$= \frac{1}{A} \begin{pmatrix} c_{00} & c_{01} & c_{02} \\ c_{10} & c_{11} & c_{12} \\ c_{20} & c_{21} & c_{22} \end{pmatrix} \cdot \begin{pmatrix} Sz_{(x,y)} \\ Szp_{(x,y)} \\ Szp_{2(x,y)} \end{pmatrix}$$

where $$A = Sp_2^3 - 2 \cdot Sp_1 \cdot Sp_2 \cdot Sp_3 + Sp_3^2 + Sp_1^2 \cdot Sp_4 - Sp_2 \cdot Sp_4 \quad (7)$$

and $$c = \begin{pmatrix} (Sp_3 \cdot Sp_3 - Sp_4 \cdot Sp_2) & (Sp_1 \cdot Sp_4 - Sp_2 \cdot Sp_3) & (Sp_2 \cdot Sp_2 - Sp_1 \cdot Sp_3) \\ (Sp_1 \cdot Sp_4 - Sp_3 \cdot Sp_2) & (Sp_2 \cdot Sp_2 - Sp_0 \cdot Sp_4) & (Sp_0 \cdot Sp_3 - Sp_1 \cdot Sp_2) \\ (Sp_2 \cdot Sp_2 - Sp_3 \cdot Sp_1) & (Sp_0 \cdot Sp_3 - Sp_2 \cdot Sp_1) & (Sp_1 \cdot Sp_1 - Sp_0 \cdot Sp_2) \end{pmatrix} \quad (8)$$

Figure 4:
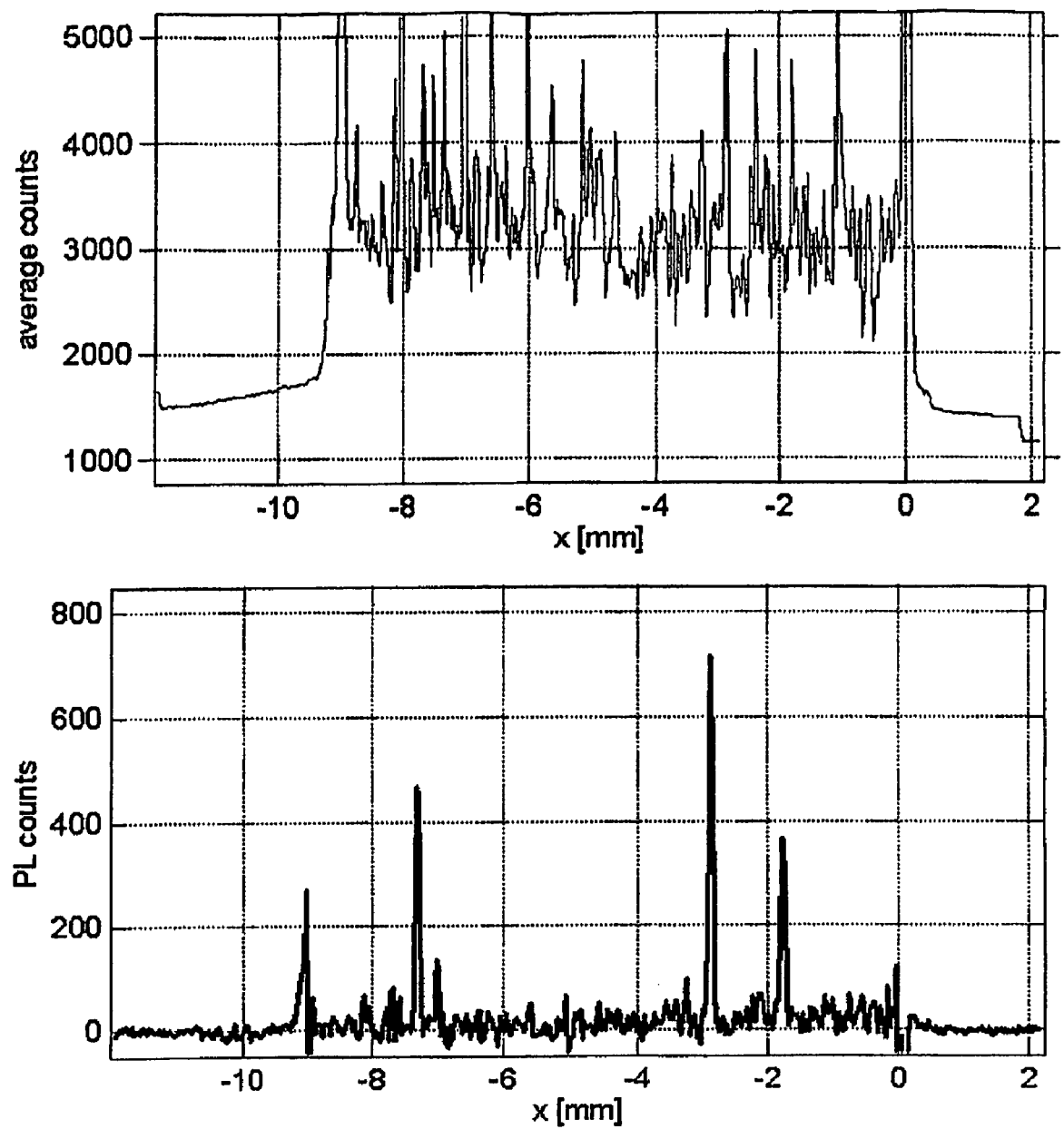
FIG. 4 shows line profiles of the data shown as images in FIG. 3 along the line y=0, at the top before and at the bottom after selection of the response signal portion that is correlated nonlinearly with the excitation light according to the method according to the invention.
Figure 5:
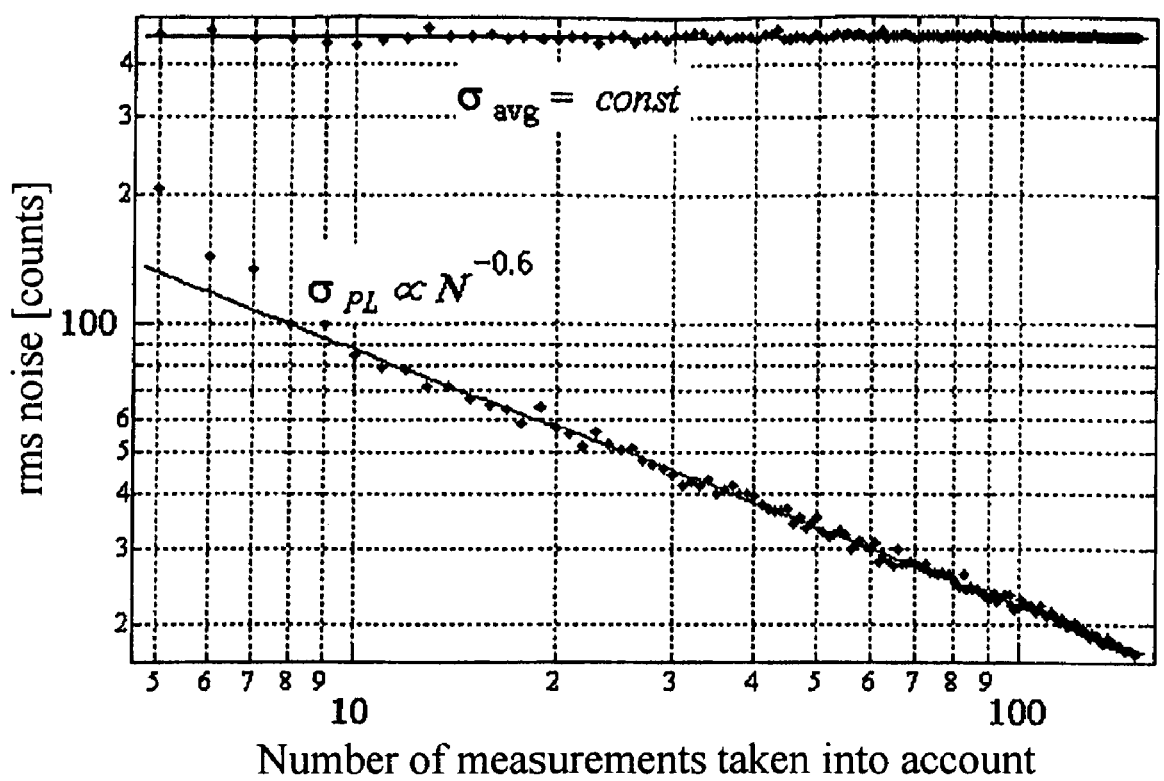
FIG. 5 shows the dependence of the spatial noise, without and after selection of the response signal portion that is correlated nonlinearly with the excitation light according to the method according to the invention, on the number of recordings taken into account for the analysis.

In the present example, a series of 150 CCD camera images, each with a (geometrically identical) image excerpt of 100×400 pixels, is analyzed with the aid of the parallel Taylor expansion. This means the creation of 40 000 quadratic fits for 6 000 000 data values. The evaluation is effected by simple matrix multiplication within a fraction of a second by means of present-day commercially available computers. The results of the analysis are illustrated in FIGS. 3 to 5.

It is advantageous that when the same power variation $P^{(n)}$ is used, only the vector $\{Sz_{(x,y)}, Szp_{(x,y)}, Szp_{2(x,y)}\}$ has to be calculated anew. The matrix $\{c_{ij}\}$, which is relatively time-consuming to calculate, and the factor A remain constant and do not have to be calculated anew even if the measurement object is changed or if a plurality of identical cycles $P^{(n)}$ are measured on one measurement object in order to improve the signal-to-noise ratio by averaging the resulting solution vectors L.

Figure 3:
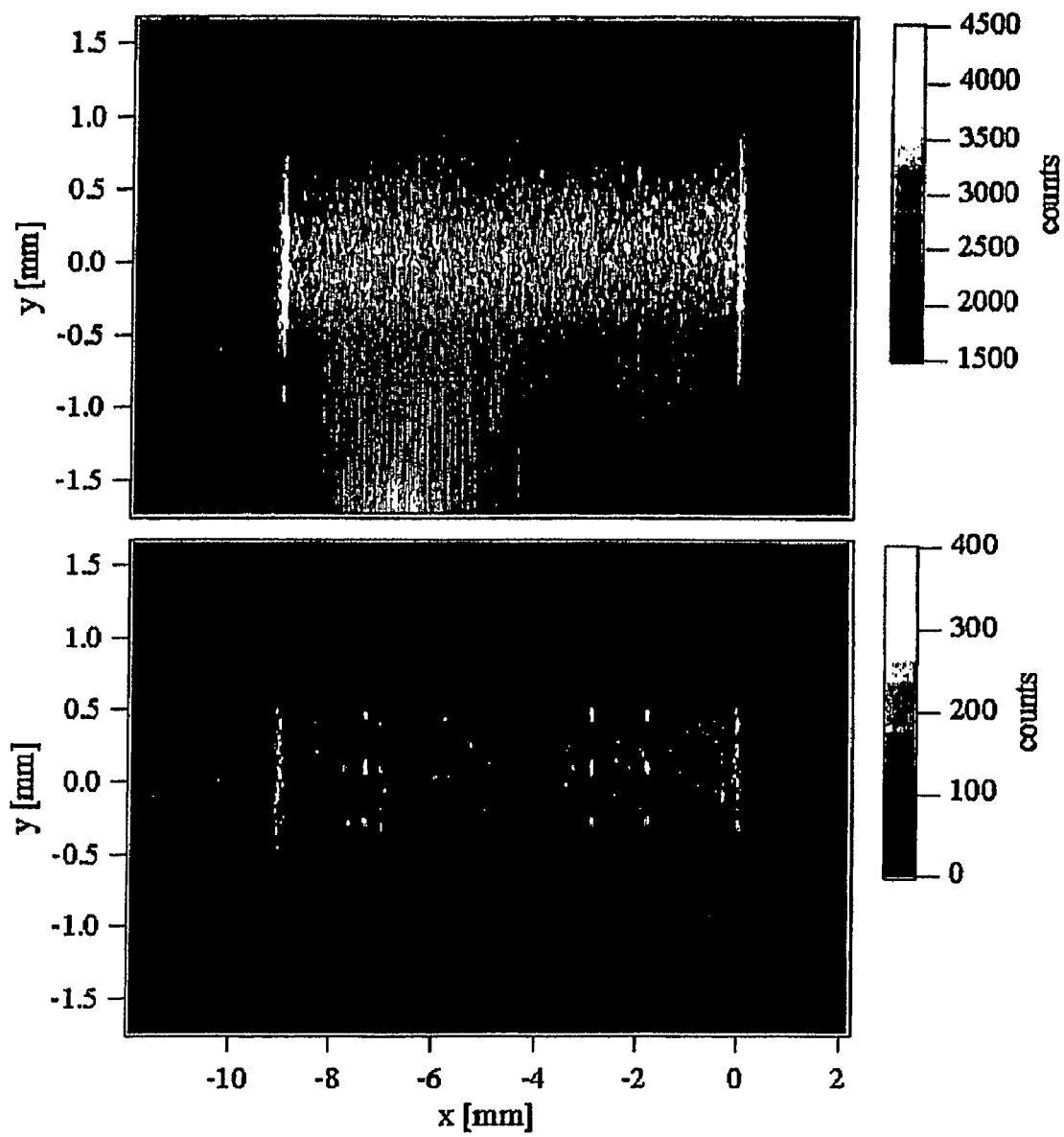
FIG. 3 shows, in a false-color representation (scale on the right-hand edge), the response signals recorded by a sensor platform in accordance with the schematic diagram of FIG. 1 as a superposition of 150 recordings with modulated intensity of the excitation light, at the top without separation of the portions that are differently correlated with the excitation light, and at the bottom after selection of the nonlinearly correlated response signal portion according to the method according to the invention.

The upper part of FIG. 3 shows the average value of a series of 150 camera images that were recorded during 1.5 rotations of the half-wave plate. An identical image is produced to a certain extent when a single image is recorded with a correspondingly long exposure time during which, without modulation of the excitation light intensity, the same total power of the excitation light is radiated in. The depiction shows exclusively scattered light portions of the excitation light, on the right-hand side (x=0 mm) at the coupling-in grating, on the left-hand side (x=−9 mm) at the coupling-out grating, in-between along the trail of the light guided in the wave-guiding film. The laser beam radiated in was expanded to approximately 1 mm parallel to the grating lines in this case.

The lower part of FIG. 3 shows the same averaged image series after the signal portions correlated linearly and those not correlated with the modulated excitation light were removed with the aid of the above-described method of parallel Taylor expansion. The depiction clearly shows at least 9 spots with immobilized dye molecules, from which emerges a nonlinear emission, in this case a luminescence excited by two-photon absorption. This emission detected in spatially resolved fashion originates from that portion of luminescence excited in the evanescent field of the waveguide which is emitted largely isotropically into the surrounding space.

A considerable portion of luminescence excited in the evanescent field is fed back into the waveguide and is guided there, there not being any preferred direction for the propagation in the waveguide. The signals that can be discerned in this part of FIG. 3 in the region of the coupling gratings probably correspond to that portion of luminescence fed back into the waveguide after two-photon excitation which is coupled out again at said coupling gratings.

FIG. 4 shows line profiles of the digitized measured values from FIG. 3 parallel to the x axis of FIG. 3 for y=0 mm. The upper line profile reveals no specific signal whatsoever, but rather only strong scattered light with a high spatially statistical variation. The lower line profile clearly reveals, in addition to the signals from the coupling gratings (at x=−9 mm and x=0 mm), the nonlinear signals from three measurement regions (spots)(at x=−7.3 mm, x=−3 mm and x=−1.8 mm). Moreover, the depiction also reveals a weaker emission (at x=−7 mm) of the same dye than at x=−7.3 mm, which was immobilized here in a lower concentration (also faintly discernible in the lower part of FIG. 3).

FIG. 5 illustrates the performance of the analytical method according to the invention on the basis of the achieved reduction of the "spatial signal noise". In this case, the "spatial signal noise" is understood to be the local variation of the signals, without any influence of a specific emission signal, that is to say the noise of the scattered and background light. In order to create this graphic diagram, an increasing number of images, up to a maximum of 150 images, were taken into account (that is to say averaged) for the analysis. The range between x=−6 nm and x=−4 nm (along y=0 nm) from FIG. 3, in which no specific emissions correlated nonlinearly with the excitation light had been ascertained, was analyzed. The number of images taken into account, when averaging the data without separation into the portions that are differently correlated with the excitation light, leads to no noise reduction whatsoever ($\sigma_{avg}$=const). It is only possible to reduce the temporal signal noise by means of longer exposure times and higher integration times (not analyzed here). By contrast, the separation of the signal components that are differently correlated with the excitation light with the aid of the parallel Taylor expansion, in accordance with the method according to the invention, leads to an ever greater reduction of the noise of the nonlinearly correlated signal portions when a larger number of images are taken into account. Taking account of 150 images already achieved a noise reduction by a factor of 25. This improvement factor can be increased even further when a larger number of images are taken into account.

3.2. Harmonic Analysis

A different approach is selected in the case of harmonic analysis. It is based on the fact that nonlinear systems generate harmonics in the case of harmonic excitation (modulation at a constant frequency). The parameters of these harmonics can be determined by Fourier analysis. Thus, a Fourier analysis can likewise be vectorized for series of images and be carried out as simple matrix multiplication, as described in the case of the analysis based on parallel Taylor expansion. Signals that are correlated linearly with the excitation light, for example of scattered light, do not contribute to higher harmonics. With the aid of this embodiment of the method according to the invention, it is possible, by way of example, upon detection of the second harmonic, to produce scattered-light-free images of luminescence signals induced by two-photon absorption.

3.3. 4-Step Algorithm

Figure 6:
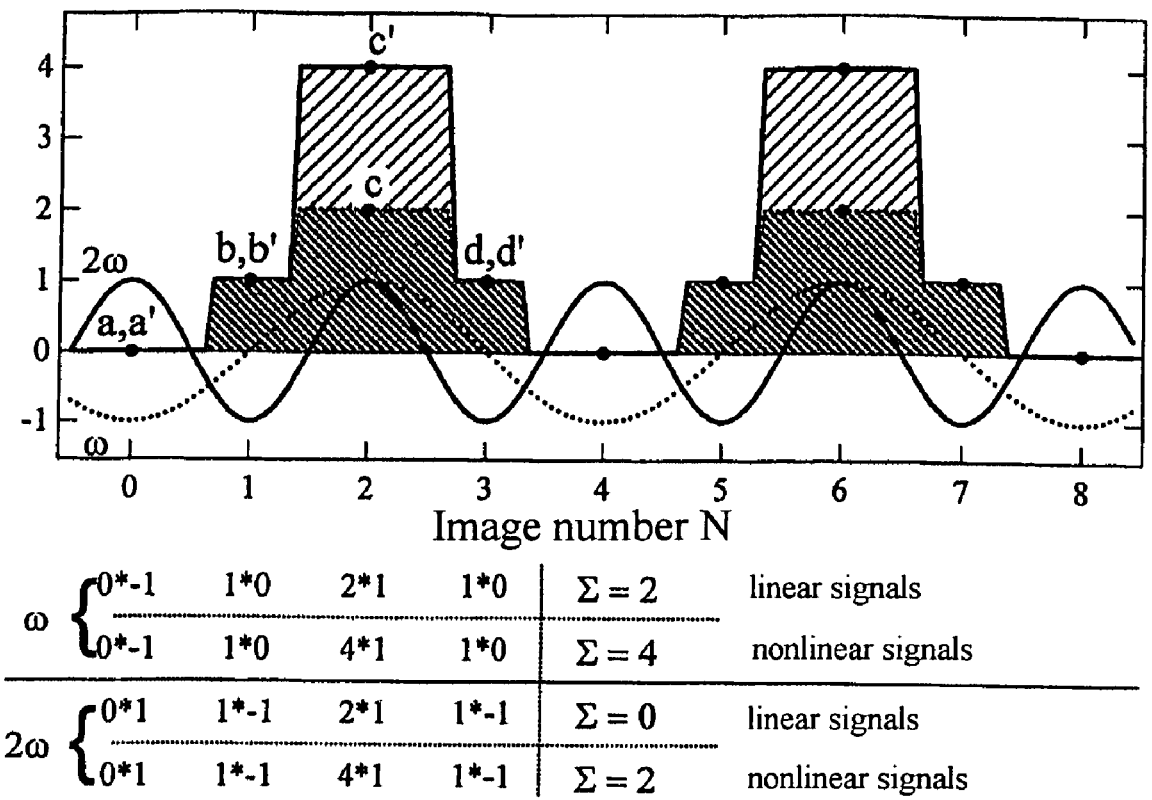
FIG. 6 illustrates an embodiment of the method according to the invention using a stepped (four-step) modulation of the excitation light and a harmonic analysis.

A variant of the embodiment using harmonic analysis that can be implemented particularly simply in practice is based on the application of a four-step algorithm. In this embodiment of the method according to the invention, the power of the excitation light is not modulated continuously at one frequency, but rather is set periodically in steps to four discrete values. The temporal profile of the signal modulation (measured here in the number of sequentially recorded camera images of the response signal) is illustrated in FIG. 6. Expressed in relative units, the intensity of the excitation light that acts on the interaction space is set sequentially to the values 0, 1, 2 and 1. This excitation light profile is followed by the linearly correlated response signal portions (e.g. of scattered light), expressed in relative units, in the same way (0, 1, 2, 1 corresponding to non-scaled values a, b, c, d), as illustrated by the closely hatched areas in FIG. 6. By way of example, the portions of emissions that are correlated quadratically with the excitation light (such as e.g. luminescence after two-photon absorption) follow the excitation light intensity, once again expressed in relative units, with the values 0, 1, 4, 1 corresponding to non-scaled values a', b', c', d'; widely hatched areas in FIG. 6.

FIG. 6 clearly reveals that the response signal detected at the fundamental frequency ($\omega$) of this stepped modulation of the excitation light contains portions correlated linearly and nonlinearly (quadratically in this case) with the excitation light. By contrast, the signal detected at the second harmonic ($2\omega$) no longer contains any linearly correlated portions (e.g. of scattered light), as becomes clear from the detailed consideration of the functioning of this embodiment of the method according to the invention:

the response signal values (0, 1, 2, 1) and (0, 1, 4, 1) measured at the different instants, correlated with the fundamental frequency and the second harmonic, respectively, are multiplied by $\cos(\omega, t)$ and $\cos(2\omega\, t)$ according to the Fourier analysis and the products are subsequently summed.

In this case, the time zero point shall be selected upon recording the signal portions c and c'. Said cos values then produce the values (−1, 0, 1, 0) for the fundamental and the values (1, −1, 1, −1) for the second harmonic, by which the signal values are to be multiplied. The embodiment of this multiplication of the measured values by the cos values, together with the formation of the sums, for determining the Fourier coefficients, for the linearly correlated signal portions (designated as "linear signals" in the table) and the nonlinearly (here quadratically) correlated signal portions (designated as "nonlinear signals" in the table), is represented in table form in FIG. 6. This reveals how, following this embodiment of the method according to the invention, the portions correlated linearly with the excitation light are eliminated upon detection according to the second harmonic.

For application in practice, it is a significant advantage that the cos values at $2\omega$ are alternately −1 and +1, that is to say that the Fourier analysis reduces to simple alternate addition and subtraction of the signal values, which significantly reduces the complexity of the numerical analysis. Even though this variant is demonstrated here only using the example of the numerical treatment for an individual measurement location, this variant of the method according to the invention can, of course, be applied to 1- or 2-dimensional images which are recorded during a corresponding stepped modulation of the excitation light and the data of which are analyzed at the second harmonic of the modulation frequency. The extremely simple algorithm proves to be particularly advantageous in particular when there are a large number of pixels.

For a quantitative analysis, the signal values of the individual pixels subsequently also have to be correspondingly scaled. If, by way of example, the scaled signal value is intended to correspond to the average value of a 4-step cycle (0, 1, 2, 1) which is measured during the first step, then the scaling factor is $$\frac{3}{4N},$$

where N is the number of measurement cycles:

$$S_{avg} = a_2 \frac{0^2 + 1^2 + 2^2 + 1^2}{4} = \frac{3}{2} \cdot a_2$$

$$S_{4\text{-}step} = a_2(0^2 - 1^2 + 2^2 - 1^2)N = 2N \cdot a_2$$

If the scaled signal value is intended to correspond to the signal which would be measured for a constant power corresponding to the average power of an entire 4-step cycle, then the scaling factor is $$\frac{1}{2N}:$$

$$S_{avg} = a_2 \left(\frac{0+1+2+1}{4}\right)^2 = a_2$$

$$S_{4\text{-}step} = a_2(0^2 - 1^2 + 2^2 - 1^2)N = 2N \cdot a_2$$

3.3.1. Correction Factors for the 4-Step Algorithm

For the case where the set excitation power which leads to the linearly correlated signal portions b and d does not exactly correspond to the average value of the excitation powers with the resulting signal portions a and c, linearly correlated signal portions (e.g. scattered light) cannot be completely suppressed by means of the method of the 4-step algorithm. A simple further development of the special variant of the method according to the invention then consists in multiplying the data corresponding to the images by a correction factor before carrying out the addition/subtraction. The corresponding correction factors for the recording of the measurement data a, b, c, d only have to be determined once for a measuring arrangement.

The multiplication factors for the 4 steps (+1, −1, +1, −1) are subsequently replaced by the correction factors $\{c_a, c_b, c_c, c_d\}$.

For the case where it is possible to measure the effective excitation power in the 4 steps, $P_a$, $P_b$, $P_c$, $P_d$, the correction factors can be determined as follows:

The background light is not correlated with the excitation light. The condition for eliminating the background light, that is to say the associated filter condition, thus reads:

$$c_a + c_b + c_c + c_d = 0 \quad (11.\text{i})$$

By contrast, the scattered light is correlated linearly with the excitation light, so that the corresponding filter condition reads:

$$c_a P_a + c_b P_b + c_c P_c + c_d P_d = 0 \quad (11.\text{ii})$$

The equation for the signal scaling (in the case of luminescence after two-photon absorption which is correlated quadratically with the excitation light) reads:

$$c_a P_a^2 + c_b P_b^2 + c_c P_c^2 + c_d P_d^2 = (P_a^2 + P_b^2 + P_c^2 + P_d^2)/3 \quad (11.\text{iii})$$

Instead of the arithmetic mean (division by 4), a value higher by 4/3 is used on the right-hand side of equation (11.iii). The cause is the signal normalization selected here (see equation (9)); however, the normalization may also be selected differently.

Therefore, three conditions are provided for determining four unknowns. The system is thus still underdetermined. This degree of freedom that still exists can be used for example to minimize the temporal noise. This is equivalent to minimizing the sum of the squares of the magnitudes, so that it is alternatively possible to use the conditions (11.iv.a) for the noise suppression of the background light or (11.iv.b) for the noise suppression of the scattered light as fourth conditions for determining the four correction factors:

$$c_a^2 + c_b^2 + c_c^2 + c_d^2 \rightarrow \min \quad (11.\text{iv.a})$$

$$c_a P_a^2 + c_b P_b^2 + c_c P_c^2 + c_d P_d^2 \rightarrow \min \quad (11.\text{iv.b})$$

For the case where the correction factors are intended to be determined from measured image data, in a corresponding image region in which no signals that are correlated nonlinearly with the excitation light should be detected, the analysis can be carried out using the condition (11.iv.b). It is advantageous if the signals of a scattering body are detected in this image region. Through iterative variation, the coefficients are adapted in such a way that the signal values $a_2$ of the 4-step algorithm in the calibration range converged toward 0, the linear portions $a_1$ at the scattering body converge toward finite values, and converge toward 0 in the rest of the calibration range, and the background values $a_0$ converge toward a constant value, or toward a smoothest possible profile, or toward the dark field values of the detector system. The convergence criteria can be defined differently depending on the application. Therefore, the procedure mentioned here is not to be understood as of a general nature, but rather only as one possible example.

3.4. Alternative Techniques

A description is given below of alternative techniques which likewise use the nonlinear character of the two-photon absorption and selected modulation methods in order to efficiently suppress background light and scattered light.

3.4.1. Pulse Duration Modulation

For most applications, the use of pulsed light sources (mode-coupled lasers) is advantageous owing to the high peak powers thereof: at the instant of the light pulse, very high excitation powers are available for a short period of time, which are sufficient for the excitation of nonlinearly correlated response signals. Particularly if the pulse duration is very short in comparison with the period of time between two successive pulses, however, it is nevertheless possible to avoid a high loading of the sample (of the interaction space) by excitation light since the acting temporal average intensity of the excitation light can be set to be relatively low.

Another possible embodiment of an analytical system according to the invention and method according to the invention that is to be performed therewith is based on varying not the intensity of the excitation light incident on the interaction space, but rather the pulse duration, for example by means of an element with an adjustable group delay dispersion (GDD). The variation of the group delay and thus the variation of the pulse duration with the pulse energy remaining the same may be effected for example by means of a Gires Tournois interferometer (GTI) mirror with an electrically controllable optical thickness.

In the cases of the examples described above, the separation of signals that are uncorrelated and correlated linearly and nonlinearly with the excitation light is based on the fact that, under the experimental conditions, the scattered light is proportional to the excitation light power and luminescence after the excitation thereof by two-photon absorption is proportional to the square of the excitation light power. For pulsed excitation, this is applicable if the power modulation is effected by variable attenuation or amplification of the entire pulse train without altering the pulse duration or the repetition rate of the pulses.

The modulation of the pulse duration is advantageously carried out such that the integral of the pulse power remains constant during the pulses, that is to say that for example in the case of shorter pulses, the peak power is correspondingly increased. Under these preconditions, the scattered light is independent of the peak power, and a luminescence induced by two-photon excitation is then linearly proportional to the pulse peak power. Consequently, the signal sought in the case of the parallel Taylor expansion is then given by the coefficient $a_1$ instead of $a_2$. In the case of harmonic analysis, the signal sought is modulated with the fundamental frequency under these conditions. One advantage of this variant of the method according to the invention is, for example, that on account of the constant average intensity, possible thermal effects, on account of possible absorption of the excitation light radiated in with a high intensity, are likewise constant and thus do not lead to any influencing of the results in a more complex manner.

A further advantage is that in the case of the two-photon absorption, when using a stepped modulation of the excitation light, it is even possible to work with only 2 steps (pulse durations), instead of 4 steps. With application of the 2-step algorithm, in an analogous manner to that described above for the 4-step algorithm, the signal values corresponding to the individual images are likewise alternately added and subtracted. In this way, it is likewise possible for the signals initiated by two-photon absorption to be selected and for the scattered light and background signal portions to be suppressed.

3.4.2. Double-Beam Excitation

As a further possible variant of an analytical system according to the invention and method according to the invention that is to be performed therewith, a double-beam excitation is distinguished by the fact that (in the case of the two-photon excitation) the two photons that are to be simultaneously absorbed need not necessarily originate from the same light source (laser) and need not necessarily have the same wavelength. If two sufficiently intense laser beams act simultaneously on the interaction space, then this results in three contributions to a two-photon absorption: one contribution is proportional to the square of the intensity of the first excitation beam, a second contribution is proportional to the square of the intensity of the second excitation beam, and a third contribution is proportional to the product of the intensities of the first and second excitation beams. In this case, the effective cross sections (the longitudes) of the three contributions may be different. It is possible, for example, for only one of the three contributions to have a significant magnitude.

If the two excitation light beams have the (different) wavelengths $\lambda_1$ and $\lambda_2$, then the excitation energy of the corresponding two-photon absorption process results from the sum of the individual photon energies. The following is thus obtained for the excitation wavelength: $\lambda_{ex} = (1/\lambda_1 + 1/\lambda_2)^{-1}$. It is advantageous if one of the two lasers is wavelength-tunable (that is to say has a variable emission wavelength). Different analytes can then be detected specifically on the basis of their two-photon absorption wavelength by means of varying the wavelength of one of the two light beams acting on the interaction space.

In order that a respective photon from the two laser beams can be absorbed simultaneously, in the case of two pulsed laser sources, both pulses must be present temporally and spatially in the interaction space. If one of the two lasers, for example a tunable laser, is a continuous wave laser (that is to say emits continuously), then the required temporal overlap is automatically ensured. In this case, the excitation light intensities used may be selected for example such that the required peak power for efficient two-photon absorption is provided with the aid of one, pulsed laser, while the continuous wave laser is used for the energy selection of the absorption transition (corresponding to the previous summation for the resulting excitation wavelength).

The methods described in section 3.1 to 3.3 can also be carried out in combination with a double-beam excitation. In this case, only luminescence from the contribution of the mixed two-photon absorption is intended to be made visible. Scattered light, and also luminescence from the two contributions of the single-beam two-photon absorption, if present, are intended to be suppressed. Following one special variant of the method according to the invention, the intensities $P_1$ and $P_2$ of the two beams are modulated independently of one another. The dependence of the measured signal then reads:

$$s = a_0 + u_1 \cdot P_1 + v_1 \cdot P_2 + u_2 \cdot P_1^2 + v_2 \cdot P_2^2 + a_2 P_1 P_2 \quad (11)$$

The coefficient $a_2$ is sought for each pixel (x,y).

In the case of the parallel Taylor expansion, the system of equations to be solved reads:

$$\frac{\partial}{\partial X_{(x,y)}} \sum_n \begin{pmatrix} s_{(x,y)}^{(n)} - a_{0_{(x,y)}} - u_{1_{(x,y)}} P_1^{(n)} - v_{1_{(x,y)}} P_2^{(n)} - \\ u_{2_{(x,y)}} P_1^{(n)2} - v_{2_{(x,y)}} P_2^{(n)2} - a_{2_{(x,y)}} P_1^{(n)} P_2^{(n)} \end{pmatrix}^2 = 0 \quad (12)$$

where $X \ldots a_0, u_1, v_1, u_2, v_2, a_2$

In the case of harmonic analysis, $P_1$ and $P_2$ are advantageously modulated with different frequencies $\omega_1$ and $\omega_2$. The signal $a_2$ sought can then be detected both at the summation frequency $(\omega_1 + \omega_2)$ and at the difference frequency $(\omega_1 - \omega_2)$.

In the case of the four-step algorithm, the intensity of the two beams $P_1$ and $P_2$ is advantageously modulated according to the values (0, 0, 1, 1) and (0, 1, 0, 1). This affords a significant advantage that simple mechanical shutters, for example rotating "choppers", can be used instead of acousto-optical, electro-optical or polarization-based modulators. By virtue of the fact that only the light path is alternately blocked and released by means of these mechanical "choppers", it is possible, as a further advantage over the abovementioned types of modulators, to completely avoid the problem of alterations of the beam position and the focusing which may arise when said modulators are used. Moreover, the theoretically optimum powers of "0%" and "100%" transmission can be realized very well using a chopper. A 50% power level is obviated here.

The evaluation of the four images is effected by summation with the coefficients (+1, −1, −1, +1). Analogously to section 3.3 and FIG. 6, the following thus result for the contributions of a 4-step cycle of $a_0, u_1, v_1, u_2, v_2, a_2$:

$a_0$: (+1)+(−1)+(−1)+(+1)=0

$u_1$: (0)+(0)+(−1)+(+1)=0

$v_1$: (0)+(−1)+(0)+(+1)=0

$u_2$: (0)+(0)+(−1)+(+1)=0

$v_2$: (0)+(−1)+(0)+(+1)=0

$a_2$: (0)+(0)+(0)+(+1)=1 \quad (13)

As a further variant of embodiments of the invention based on a double-beam technique, the modulation of the intensity of one or both beams may be replaced by the modulation of a different beam parameter, for example the pulse duration or the spatial position.

4. Application to Further Nonlinear Optical Processes

Various embodiments of an analytical system according to the invention and methods that are to be performed therewith have been explained above primarily using examples for application to luminescence excitation by two-photon absorption. However, the invention can also be applied to other nonlinear optical processes, as will be demonstrated below.

4.1. Multiphoton Excitation

In the case of multiphoton excitation, the dependence of the luminescence signal on the excitation power is given by:

$$s = a_0 + a_1 \cdot P + a_m \cdot P^m$$

if m photons are absorbed simultaneously. An excitation by multiphoton absorption of the order m then corresponds to a linear absorption (one-photon absorption) at a wavelength $\lambda_{ex} = \lambda_L/m$ if the wavelength of the excitation laser is $\lambda_L$. At an excitation wavelength of 800 nm, multiphoton absorptions can be effected by means of correspondingly selected dyes or chromophores thus with transition energies corresponding to wavelengths of 800 nm, 400 nm, 267 nm, 200 nm, etc.

The parallel Taylor expansion is implemented analogously to section 3.1 or 3.4.1. In this case, the portions of luminescence after one-, two-, three-, m-photon absorption can be correspondingly separated. In this case, the portion of one-photon absorption cannot be separated from excitation scattered light that is linearly correlated with the excitation light intensity. However, all the remaining higher-order portions (corresponding to multiphoton processes) can be separated from the scattered light and also among one another.

When using harmonic analysis, it must be taken into consideration that processes of different orders that occur simultaneously usually cannot be separated in a simple form. The luminescence induced by five-photon absorption, for example, contains Fourier components at the modulation frequency of the excitation light ($\omega$), and also at the harmonics $2\omega$, $3\omega$, $4\omega$ and $5\omega$. The signal strength additionally decreases as the order of the harmonics increases. It follows from this that a detection system for m-photon absorption is best to be operated at the second harmonic. Moreover, as far as possible no light from other nonlinear processes should be registered by the detection system. If nonlinear-optical signals of the order k are nevertheless measured by the detector, the harmonic analysis should be effected at the k+1-th harmonic. Trivially, it is necessary, of course, for $m \geq k+1$ to hold true.

The method of modulation and signal recording by means of a 4-step algorithm can be transferred without any change from two-photon processes to multiphoton processes. Only the scaling factors for the signals have to be adapted.

It is also part of the present invention that, in the case of detection of m-photon absorption, up to m laser beams are used in order to realize a selective analysis analogously to the above described arrangement of the double-beam excitation.

4.2. Frequency Doubling, Summation and Differential Frequency Generation

The text above has presented applications to those processes which are to be referred to as "resonant processes" in the context of the present invention. They are to be understood to mean those processes by means of which a really existing state, for example an excited state of a molecule or chromophore, is attained (excited)(e.g. by multiphoton absorption), which state then decays again after a finite, albeit usually short time duration for example through emission of light. In contrast thereto, "non-resonant processes" are to be understood as those processes in which an excited state does not really exist, but rather is of a purely virtual nature. This means that the virtual excited state has to decay again as it were instantaneously, additional boundary conditions having to be taken into account for direction and pulse of the light beams involved.

For the generation and analysis of the signals according to the present invention, however, it is unimportant in this case whether virtual or real processes are involved in the excitation process. The analytical systems according to the invention and methods to be performed therewith can be applied in an analogous manner to the signal generation, signal detection and signal analysis of nonlinear processes which lead to really existing or to virtually excited states.

In this case, for example for the analysis of frequency doubling ("second harmonic generation"), the same procedure is to be adopted as above for the generation of luminescence by two-photon absorption, for single-beam excitation. The variants of the method according to the invention that are described in sections 3.1. to 3.3. can be applied directly to this, without any change.

An arrangement and analysis for summation frequency generation can be operated analogously to the variant of double-beam excitation as described in section 3.4.2.

An exemplary application for a two-dimensional nonlinearly optical signal detection is the measurement of the homogeneity of frequency doubling crystals. The angle between the light beam of the excitation laser and the frequency-doubled light beam generated is usually 0 or very small, so that a spatial separation of the two light beams is scarcely possible. For the selective detection of the doubled signals with the aid of conventional arrangements and methods, it is therefore necessary to use highly effective spectral filters, or the use of spectrally dispersive elements (grating, prism) is required, in which case only one spatial dimension can be resolved, while it is no longer possible to generate two-dimensional images. A further disadvantage of the conventional arrangements and methods is, moreover, that the excitation light usually has to be focused into the crystal in order to achieve the required intensity for efficient frequency doubling. In order to generate a two-dimensional representation of the generation of the frequency-doubled signals, it is then necessary to scan the focused excitation light over the cross-sectional area of the crystal. This is not only associated with a higher expenditure of time, but also inherently includes within itself the uncertainty that it is difficult to distinguish between inhomogeneities of the frequency-doubling crystal and changes in the optical light path for different focusing points in the scanning plane as a cause of possible variations of the frequency-doubled signal.

With the aid of the analytical system and method according to the invention, it would be possible to eliminate a crystal with an expanded excitation light beam and to detect a two-dimensional image of the frequency-doubled signals generated at different regions of the crystal. Owing to the beam expansion, for such an arrangement the frequency-doubled signals will generally be very small and provided with strong portions of the excitation light. The detection methods described here were developed precisely for this problem. All of the abovementioned embodiments of the invention are suitable for the separation of the signal portions that are differently correlated with the excitation light. For this specific application in which the ratio of frequency-doubled signal portions to be expected and of signal portions of the fundamental frequency radiated in is particularly unfavorable, an embodiment of the invention will preferably be used in combination with such a spectral filtering, e.g. with the aid of a bandpass filter, in which the spatially resolved information about the signal distribution is preserved.

The invention claimed is:

1. A method for highly sensitive simultaneous measurement of nonlinear optical emission signals, spatially resolved in one or two spatial dimensions, comprising:
    radiating excitation light from at least one light source in a power-modulated and/or pulse-duration-modulated form into interaction spaces, in each of which one or a plurality of emissions that are correlated nonlinearly with the excitation light can be excited,
    measuring light emerging from said interaction spaces by means of a one- or two-dimensional detector array,
    transmitting measurement data from said detector array to a computer and formatting the data in a one- or multidimensional data matrix,
characterized in that data representative of those portions of the light emerging from the interaction spaces which are linearly proportional to the intensity of the excitation light available in the interaction spaces are separated from data representative of the portions of the light emerging from the interaction spaces which are nonlinearly proportional to the available excitation light intensity.

2. The method as claimed in claim 1, wherein the method does not comprise any spectral filtering of the light that is to be detected and emerge from the interaction spaces.

3. The method as claimed in claim 1, wherein the method is carried out in combination with a spectral filtering of the light that is to be detected and emerge from the interaction spaces.

4. The method as claimed in claim 1, wherein said one- or two-dimensional detector array is selected from the group consisting of CCD cameras, CCD chips, CMOS cameras, CMOS chips, photodiode arrays, avalanche diode arrays, multichannel plates and multichannel photomultipliers, wherein a phase-sensitive demodulation is capable of being integrated into said detector array.

5. The method as claimed in claim 1, wherein the modulation of the excitation light radiated into an interaction space is effected by means of optomechanical and/or acousto-optical and/or electro-optically active auxiliary means.

6. The method as claimed in claim 5, wherein said optomechanical and/or acousto-optical and/or electro-optically active auxiliary means are selected from the group consisting of mechanical shutters and rotating choppers which in each case alternately block and release the light path between the excitation light source and the interaction space, polarization-selective components that are locally or temporally variable in terms of their transmission, acousto-optical modulators and modulators based on interference effects.

7. The method as claimed in one of claims 1, wherein the modulation of the excitation light radiated into an interaction space is effected by means of direct, active modulation of the light radiated from the excitation light source.

8. The method as claimed in claim 7, wherein the modulation of the excitation light radiated into an interaction space is effected by means of modulation of the excitation current of a semiconductor laser as excitation light source.

9. The method as claimed in claim 1, wherein the modulation of the excitation light radiated into an interaction space is effected periodically.

10. The method as claimed in claim 1, wherein the modulation of the excitation light radiated into an interaction space is effected non-periodically.

11. The method as claimed in claim 1, wherein the modulation of the excitation light radiated into an interaction space consists of modulation of the intensity radiated in.

12. The method as claimed in claim 1, wherein the modulation of the excitation light radiated into an interaction space consists of the simultaneous modulation of the pulse duration and the peak power of the excitation light radiated in.

13. The method as claimed in claim 1, wherein the method is effected without detection of the modulated excitation light or a measurement variable proportional thereto.

14. The method as claimed in claim 1, wherein, in addition to the detection of the light emerging from the interaction spaces, the detection of the modulated excitation light or a measurement variable proportional thereto is detected.

15. The method as claimed in claim 1, wherein the detection of the light emerging from the interaction spaces is effected temporally correlated with the modulation of the excitation light power.

16. The method as claimed in claim 15, wherein the detection of the light emerging from the interaction spaces is effected with a frequency corresponding to an integer multiple of the modulation frequency of the excitation light power.

17. The method as claimed in 1, wherein the separation of the data representative of the portions of the light emerging from the interaction spaces which are nonlinearly proportional to the excitation light power from the data representative of the remaining portions of said light is effected using a parallel series expansion.

18. The method as claimed in claim 1, wherein the separation of the data representative of the portions of the light emerging from the interaction spaces which are nonlinearly proportional to the excitation light power from the data representative of the remaining portions of said light is effected using a parallel Taylor expansion.

19. The method as claimed in claim 1, wherein the separation of the data representative of the portions of the light emerging from the interaction spaces which are nonlinearly proportional to the excitation light power from the data representative of the remaining portions of said light is effected using a harmonic analysis.

20. The method as claimed in claim 1, wherein the separation of the data representative of the portions of the light emerging from the interaction spaces which are nonlinearly proportional to the excitation light power from the data representative of the remaining portions of said light is effected by means of a stepped modulation of the excitation light power.

21. The method as claimed in claim 1, wherein the separation of the data representative of the portions of the light emerging from the interaction spaces which are nonlinearly proportional to the excitation light power from the data representative of the remaining portions of said light is effected using a four-step algorithm for the modulation of the excitation light power.

22. The method as claimed in 1, wherein in case of a modulation of the excitation light power experimentally dictated deviations of the excitation light powers from the desired values provided for the modulation are compensated for using numerical corrections.

23. The method as claimed in claim 21, wherein the data representative of the light emerging from the interaction spaces obtained using a four-step algorithm for the modulation are multiplied by correction factors.

24. The method as claimed in claim 23, wherein the correction factors are determined from measured excitation light powers.

25. The method as claimed in claim 23, wherein the correction factors are determined by a numerical analysis of the data representative of the light emerging from the interaction spaces generated.

26. The method as claimed in claim 1, wherein the separation of the data representative of the portions of the light emerging from the interaction spaces which are nonlinearly proportional to the excitation light power from the data representative of the remaining portions of said light is effected in real time contemporaneously with the recording of the signals from the interaction space.

27. The method as claimed in claim 1, wherein the interaction space is an interaction layer at a surface of a fixed carrier, the areal extent of said interaction layer being defined by the interaction area with the impinging power-modulated excitation light and its depth being defined by the range of the modulated excitation light intensity in this space dimension perpendicular to said surface of the carrier.

28. The method as claimed in claim 27, wherein compounds or substances or molecular subgroups are situated within the interaction space which, under the action of the excitation light, are capable of emitting optical signals correlated nonlinearly therewith, or with the aid of which, after the interaction thereof with further compounds present in the interaction space, optical signals correlated nonlinearly with the excitation light can be generated.

29. The method as claimed in claim 27, wherein one or a plurality of specific binding partners for the detection of one or a plurality of analytes are immobilized on the surface of said fixed carrier in a binding assay, the analyte detection being effected on the basis of an optical response signal, correlated nonlinearly with the excitation light power, of the immobilized binding partner itself or of a binding partner supplied in solution for binding to the immobilized binding partner or of one or a plurality of further binding partners supplied in one or a plurality of additional method steps.

30. The method as claimed in claim 29, wherein the specific binding partners immobilized on the surface of said fixed carrier are the one or the plurality of analytes themselves which are immobilized, wherein the one or the plurality of analytes are embedded in a native sample matrix or in a sample matrix that is modified by one or a plurality of conditioning steps.

31. The method as claimed in claim 29, wherein the specific binding partners immobilized on the surface of said fixed carrier are biological or biochemical or synthetic identification elements for the specific identification of one or a plurality of analytes situated in a supplied sample.

32. The method as claimed in claim 29, wherein said binding partners are selected from the group consisting of proteins, peptides, enzymes, glycopeptides, oligosaccharides, lectins, antigens for antibodies, proteins functionalized with additional binding sites, nucleic acids, nucleic acid analogs, aptamers, membrane-bound and isolated receptors and ligands thereof, cavities produced by chemical synthesis for receiving molecular imprints, natural polymers and synthetic polymers.

33. The method as claimed in claim 28, wherein the compounds or substances or molecular subgroups are applied on the surface of said fixed carrier, and are immobilized in discrete measurement regions which may have an arbitrary geometry wherein an individual measurement region can optionally contain identical or different compounds or substances or molecular subgroups or specific binding partners.

34. The method as claimed in claim 33, wherein discrete measurement regions are produced by spatially selective application of specific binding partners on said fixed carrier or of compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated.

35. The method as claimed in claim 33, wherein there are applied between the spatially separate measurement regions or in unoccupied partial regions within said measurement regions compounds that are chemically neutral with respect to the analytes and/or with respect to binding partners.

36. The method as claimed in claim 28, wherein, at the surface of said fixed carrier, the compounds or substances or molecular subgroups are applied, or specific binding partners are applied wherein such are immobilized directly or by means of a spacer formed as an independent molecule or molecular group at the surface of said fixed carrier, with utilization of one or a plurality of types of interactions from the group of interactions consisting of hydrophilic interactions, electrostatic interactions and covalent binding.

37. The method as claimed in claim 28, wherein an adhesion promoting layer is applied between the surface of said fixed carrier and the immobilized compounds or substances or molecular subgroups or the applied specific binding partners.

38. The method as claimed in claim 33, wherein more than 10 measurement regions are arranged on a square centimeter in a two-dimensional arrangement on the surface of said fixed carrier.

39. The method as claimed in claim 27, wherein said fixed carrier is optically transparent at the wavelength of an acting excitation light.

40. The method as claimed in one of claim 27, wherein said fixed carrier is essentially planar.

41. The method as claimed in claim 27, wherein said fixed carrier comprises an optical waveguide structure comprising one or a plurality of layers.

42. The method as claimed in claim 27, wherein said fixed carrier comprises a planar optical waveguide that is continuous or divided into discrete wave-guiding regions comprising one or a plurality of layers.

43. The method as claimed in claim 27, wherein said fixed carrier comprises a planar optical thin-film waveguide with an essentially optically transparent, wave-guiding layer (a) on a second, essentially optically transparent layer (b) having a lower refractive index than layer (a) and optionally an essentially optically transparent intermediate layer (b') between layer (a) and layer (b) having a lower refractive index than layer (a).

44. The method as claimed in claim 41, wherein a wave-guiding layer of said fixed carrier is in optical contact with one or a plurality of optical coupling elements which enable excitation light to be coupled into said wave-guiding layer, said optical coupling elements being selected from the group consisting of prism couplers, evanescent couplers with united optical waveguides with overlapping evanescent fields, end face couplers with focusing lenses arranged before an end side of said wave-guiding layer of the evanescent field sensor platform, and grating couplers.

45. The method as claimed in claim 41, wherein a wave-guiding layer of the fixed carrier comprises one or a plurality of grating structures (c) which enable excitation light to be coupled in.

46. The method as claimed in claim 45, wherein a wave-guiding layer of the fixed carrier comprises one or a plurality of grating structures (c') having an identical or different grating period and grating depth with respect to grating structures (c) and enable light guided in said wave-guiding layer to be coupled out.

47. The method as claimed in claim 1, wherein said data representative of the portion of the light emerging from the interaction spaces which are nonlinearly proportional to the excitation light intensity comprise the data representative of signals of a frequency doubling, summation or differential frequency generation.

48. The method as claimed in claim 1, wherein said data representative of the portion of the light emerging from the interaction spaces which are nonlinearly proportional to the excitation light intensity are induced by a multi-photon absorption.

49. The method as claimed in claim 48, wherein said multiphoton absorption is a two-photon absorption.

50. An analytical system for highly sensitive simultaneous measurement of nonlinear optical emission signals, spatially resolved in one or two spatial dimensions, comprising:
   at least one light source for emitting excitation light,
   technical auxiliary means for power modulation and/or pulse duration modulation of the excitation light emerging from the at least one light source,
   an interaction volume or an interaction area or an interaction layer, designated jointly as interaction space, wherein one or a plurality of emissions that are correlated nonlinearly with the excitation light can be excited,
   at least one one- or two-dimensional detector array for measuring the light emerging from the interaction space,
   a computer to which the measurement data of said detector arrays are transmitted and with the aid of which the measurement data are formatted in a one- or multidimensional data matrix and analyzed,
wherein data representative of those portions of the light emerging from the interaction spaces which are linearly proportional to the intensity of the excitation light available in the interaction spaces are separated from data representative of the portions of the light emerging from the interaction spaces which are nonlinearly proportional to the available excitation light intensity.

51. The analytical system as claimed in claim 50, wherein the method does not comprise any components for a spectral filtering of the light that is to be detected and emerge from the interaction spaces.

52. The analytical system as claimed in claim 50, wherein the method additionally comprises components for a spectral filtering of the light that is to be detected and emerge from the interaction spaces.

53. The analytical system as claimed in claim 50, wherein at least one one- or two-dimensional detector array is selected from the group consisting of CCD cameras, CCD chips, CMOS cameras, CMOS chips, photodiode arrays, avalanche diode arrays, multichannel plates and multichannel photomultipliers, such that a phase-sensitive demodulation is capable of being integrated into said detector array.

54. The analytical system as claimed in claim 50, wherein said technical auxiliary means for the modulation of the excitation light radiated in to an interaction space are selected from the group consisting of optomechanical, acousto-optical and electro-optically active auxiliary means.

55. The analytical system as claimed in claim 54, wherein said optomechanical and/or acousto-optical and/or electro-optically active auxiliary means are selected from the group consisting of mechanical shutters and rotating choppers which in each case alternately block and release the light path between the excitation light source and the interaction space, polarization-selective components, acousto-optical modulators and modulators based on interference effects.

56. The analytical system as claimed in claim 50, wherein the modulation of the excitation light radiated into an interaction space is effected by means of direct, active modulation of the light radiated from the excitation light source.

57. The analytical system as claimed in claim 56, wherein the modulation of the excitation light radiated in to an interaction space is effected by means of modulation of the excitation current for a semiconductor laser as excitation light source.

58. The analytical system as claimed in claim 50, wherein the modulation of the excitation light radiated into an interaction space is effected periodically.

59. The analytical system as claimed in claim 50, wherein the modulation of the excitation light radiated into an interaction space is effected non-periodically.

60. The analytical system as claimed in claim 50, wherein the modulation of the excitation light radiated into an interaction space consists of modulation of the intensity radiated in.

61. The analytical system as claimed in claim 50, wherein the modulation of the excitation light radiated into an interaction space consists of simultaneous modulation of pulse duration and peak power of the excitation light radiated in.

62. The analytical system as claimed in claim 50, wherein the system is effected without detection of the modulated excitation light or a measurement variable proportional thereto.

63. The analytical system as claimed claim 50, wherein the system comprises, in addition to the detection of the light emerging from the interaction spaces, a detection of the modulated excitation light or a measurement variable proportional thereto.

64. The analytical system as claimed in claim 50, wherein the detection of the light emerging from the interaction spaces is effected in a manner temporally correlated with the modulation of the excitation light power.

65. The analytical system as claimed in claim 64, wherein the detection of the light emerging from the interaction spaces is effected with a frequency corresponding to an integer multiple of the modulation frequency of the excitation light power.

66. The analytical system as claimed in claim 50, wherein the separation of the data representative of the portions of the light emerging from the interaction spaces which are nonlinearly proportional to the excitation light power from the data representative of the remaining portions of said light is effected using a parallel series expansion.

67. The analytical system as claimed in claim 50, wherein the separation of the data representative of the portions of the light emerging from the interaction spaces which are nonlinearly proportional to the excitation light power from the data representative of the remaining portions of said light is effected using a harmonic analysis.

68. The analytical system as claimed in claim 50, wherein the separation of the data representative of the portions of light emerging from the interaction spaces which are nonlinearly proportional to the excitation light power from the data representative of the remaining portions of said light is effected using a stepped modulation of the excitation light power.

69. The analytical system as claimed in claim 50, wherein the separation of the data representative of the portions of light emerging from the interaction spaces which are nonlinearly proportional to the excitation light power from the data representative of the remaining portions of said light is effected using a four-step algorithm for the modulation of the excitation light power.

70. The analytical system as claimed in claim 50, wherein the interaction space is an interaction layer at a surface of a fixed carrier, the areal extent of the interaction layer being defined by the interaction area with the impinging power-modulated excitation light and its depth being defined by the range of the modulated excitation light intensity in this space dimension perpendicular to said surface of the carrier.

71. The analytical system as claimed in claim 70, wherein there are situated within the interaction space compounds or substances or molecular subgroups which, under the action of the excitation light, are capable of emitting optical signals correlated nonlinearly therewith, or with the aid of which, after the interaction thereof with further compounds present in the interaction space, optical signals correlated nonlinearly with the excitation light can be generated.

72. The analytical system as claimed in claim 70, wherein there are immobilized on the surface of said fixed carrier one or a plurality of specific binding partners for the detection of one or a plurality of analytes in a binding assay the analyte detection being effected using an optical response signal, correlated nonlinearly with the excitation light power, of the immobilized binding partner itself or of the binding partner supplied in solution for binding to the immobilized binding partner or of one or a plurality of further binding partners supplied in one or a plurality of additional method steps.

73. The analytical system as claimed in claim 72, wherein the specific binding partners immobilized on the surface of said fixed carrier are the one or the plurality of analytes themselves which are immobilized, wherein the specific binding partners are embedded in a native sample matrix or in a sample matrix that is modified by one or a plurality of conditioning steps.

74. The analytical system as claimed in claim 72, wherein the specific binding partners immobilized on the surface of said fixed carrier are biological or biochemical or synthetic identification elements for the specific identification of one or a plurality of analytes situated in a supplied sample.

75. The analytical system as claimed in claim 72, wherein said binding partners are selected from the group consisting of proteins, peptides, enzymes, glycopeptides, oligosaccharides, lectins, antigens for antibodies, proteins functionalized with additional binding sites, nucleic acids, nucleic acid analogs, aptamers, membrane-bound and isolated receptors and ligands thereof, cavities produced by chemical synthesis for receiving molecular imprints, natural polymers and synthetic polymers.

76. The analytical system as claimed in claim 71, wherein the compounds or substances or molecular subgroups are applied on the surface of said fixed carrier, and are immobilized in discrete measurement regions which may have an arbitrary geometry, wherein an individual measurement region can optionally contain identical or different compounds or substances or molecular subgroups or specific binding partners.

77. The analytical system as claimed in claim 76, wherein more than 10 measurement regions are arranged on a square centimeter in a two-dimensional arrangement on the surface of said fixed carrier.

78. The analytical system as claimed in claim 70, wherein said fixed carrier is optically transparent at a wavelength of an acting excitation light.

79. The analytical system as claimed in claim 70, wherein said fixed carrier is essentially planar.

80. The analytical system as claimed in claim 70, wherein said fixed carrier comprises an optical waveguide structure, comprising one or a plurality of layers.

81. The analytical system as claimed in claim 70, wherein said fixed carrier comprises a planar optical waveguide that is continuous or divided into discrete wave-guiding regions and comprises one or a plurality of layers.

82. The analytical system as claimed in claim 70, wherein said fixed carrier comprises a planar optical thin-film waveguide with an essentially optically transparent, waveguiding layer (a) on a second, essentially optically transparent layer (b) having a lower refractive index than layer (a) and optionally an essentially optically transparent intermediate layer (b') between layer (a) and layer (b) having a lower refractive index than layer (a).

83. The analytical system as claimed in claim 80, wherein a wave-guiding layer of said fixed carrier is in optical contact with one or a plurality of optical coupling elements which enable excitation light to be coupled into said wave-guiding layer, said optical coupling elements being selected from the group of consisting of prism couplers, evanescent couplers with united optical waveguides with overlapping evanescent fields, end face couplers with focusing lenses arranged before an end side of said wave-guiding layer of the evanescent field sensor platform, and grating couplers.

84. The analytical system as claimed in claim 80, wherein a wave-guiding layer of the fixed carrier comprises one or a plurality of grating structures (c) which enable excitation light to be coupled in.

85. The analytical system as claimed in claim 80, wherein a wave-guiding layer of the fixed carrier comprises one or a plurality of grating structures (c') having an identical or different grating period and grating depth with respect to grating structures (c) and enable light guided in said wave-guiding layer to be coupled out.

86. The analytical system as claimed in claim 50, wherein said portions of the light emerging from the interaction spaces which are nonlinearly proportional to the excitation light intensity comprise the signals of a frequency doubling, summation or differential frequency generation.

87. The analytical system as claimed in claim 50, wherein said data representative of the portion of the light emerging from the interaction spaces which are nonlinearly proportional to the excitation light intensity are induced by a multiphoton absorption.

88. The analytical system as claimed in claim 87, wherein said multiphoton absorption is a two-photon absorption.

* * * * *